(12) United States Patent
Parker et al.

(10) Patent No.: US 12,324,922 B2
(45) Date of Patent: Jun. 10, 2025

(54) LEAD ANCHOR

(71) Applicant: Saluda Medical Pty Limited, Artarmon (AU)

(72) Inventors: John Louis Parker, Artarmon (AU); Richard James Oldfield, Artarmon (AU)

(73) Assignee: Saluda Medical Pty Limited, Macquarie Park (AU)

( * ) Notice: Subject to any disclaimer, the term of this patent is extended or adjusted under 35 U.S.C. 154(b) by 781 days.

(21) Appl. No.: 17/412,001

(22) Filed: Aug. 25, 2021

(65) Prior Publication Data

US 2022/0080211 A1 Mar. 17, 2022

(30) Foreign Application Priority Data

Sep. 16, 2020 (AU) ................................ 2020903311

(51) Int. Cl.
*A61N 1/375* (2006.01)

(52) U.S. Cl.
CPC ................................ *A61N 1/37518* (2017.08)

(58) Field of Classification Search
CPC .......................... A61N 1/37518; A61N 1/0558
See application file for complete search history.

(56) References Cited

U.S. PATENT DOCUMENTS

| 4,276,882 | A | * | 7/1981 | Dickhudt | A61N 1/057 |
| | | | | | 607/9 |
| 4,471,159 | A | * | 9/1984 | Frank, Jr. | H01R 4/44 |
| | | | | | 411/452 |
| 8,954,165 | B2 | | 2/2015 | Sharma et al. | |
| 9,887,470 | B2 | | 2/2018 | Nguyen-Stella et al. | |
| 2013/0204336 | A1 | * | 8/2013 | Sharma | A61N 1/0558 |
| | | | | | 607/117 |
| 2014/0343646 | A1 | * | 11/2014 | Leven | A61N 1/0558 |
| | | | | | 607/116 |
| 2015/0045865 | A1 | * | 2/2015 | Nageri | A61N 1/0558 |
| | | | | | 607/116 |

* cited by examiner

*Primary Examiner* — Eugene T Wu
(74) *Attorney, Agent, or Firm* — Barnes & Thornburg LLP

(57) ABSTRACT

A lead anchor (1) to secure a stimulation lead (3) with an internal lead lumen (5), the lead anchor (1) comprising: a first clamp surface (7); a second clamp surface (9) opposed to the first clamp surface (7); and an adjustable fastener (11) to selectively draw the first clamp surface (7) towards the second clamp surface (9) to secure the stimulation lead (3) located between the first clamp surface (7) and the second clamp surface (9), wherein the first clamp surface (7) and the second clamp surface (9) are profiled to apply clamping force (13) to secure the stimulation lead (3) while maintaining an open internal lead lumen (5).

12 Claims, 20 Drawing Sheets

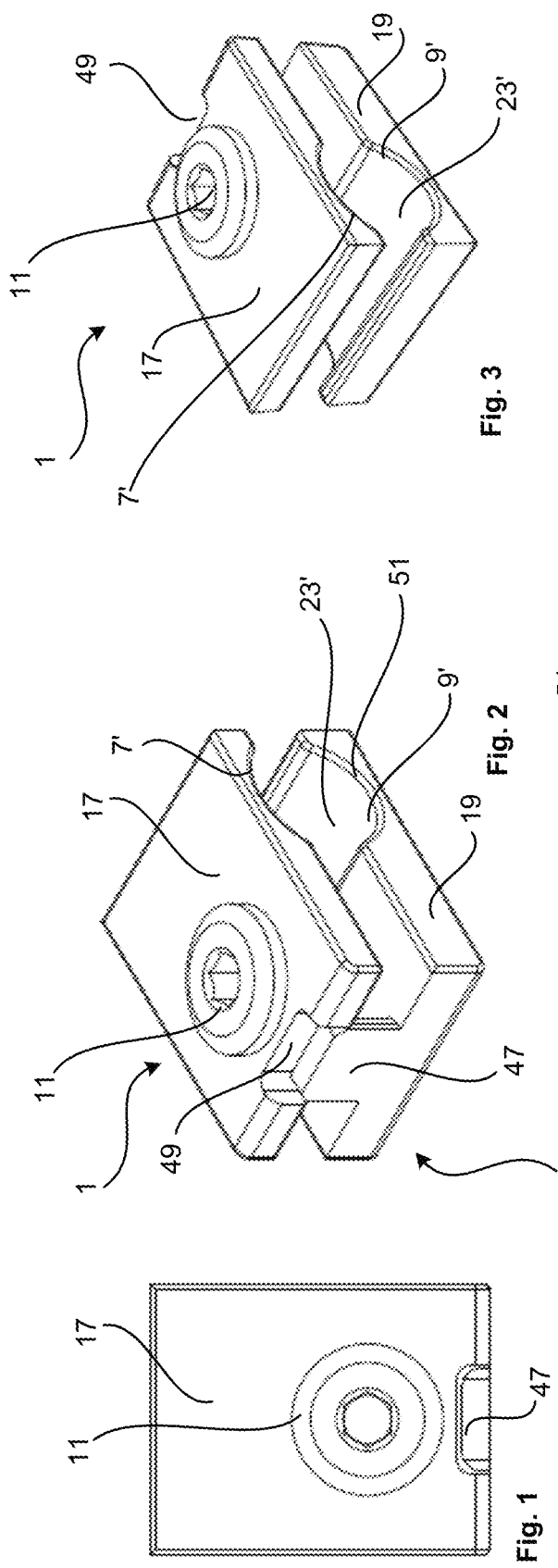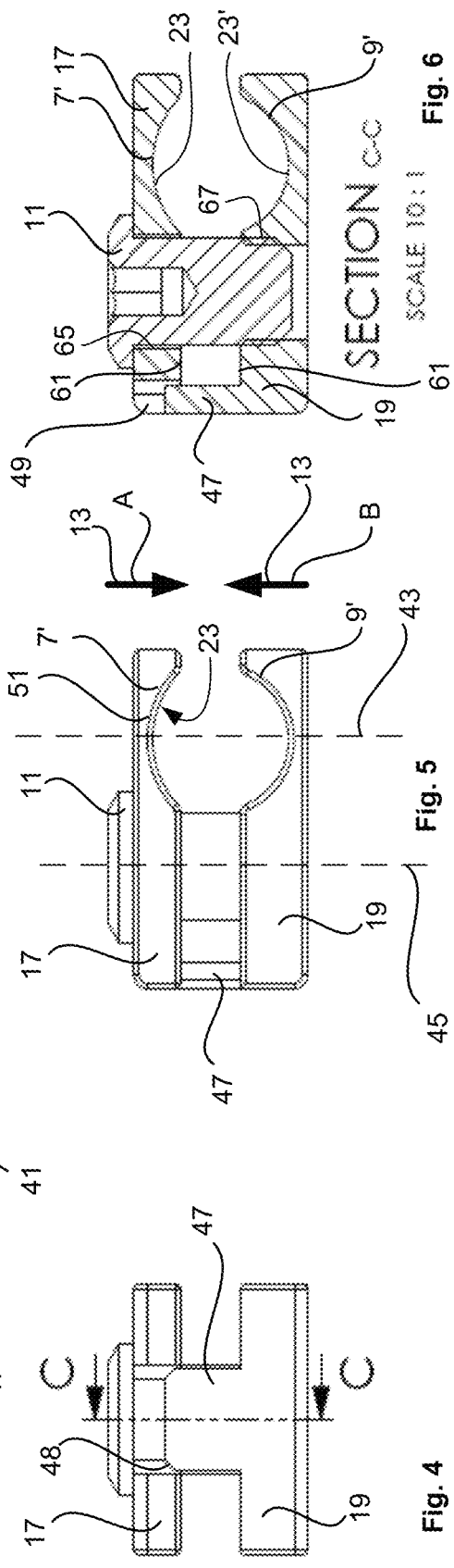

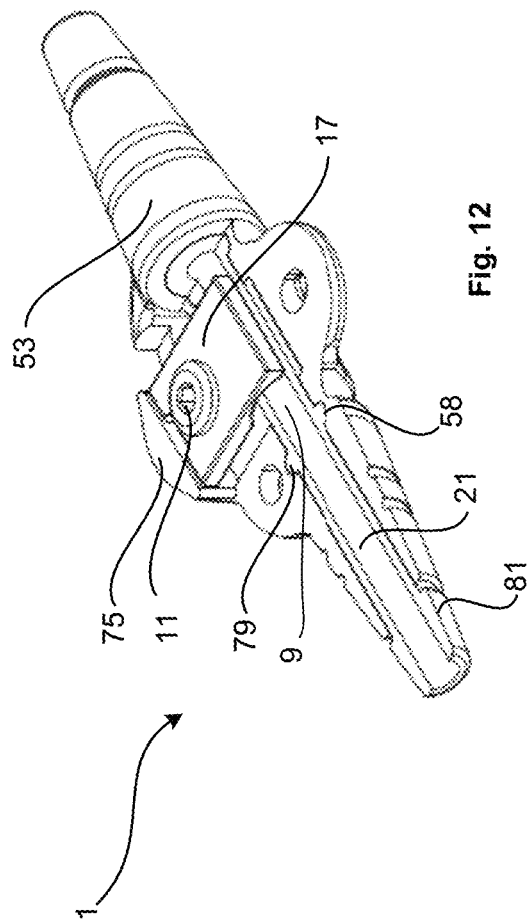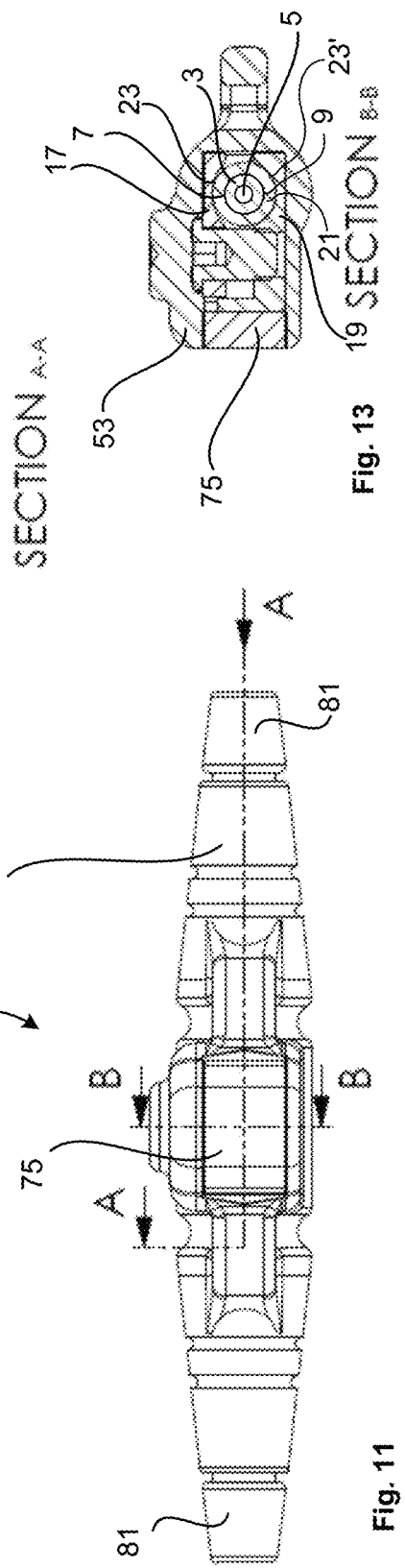

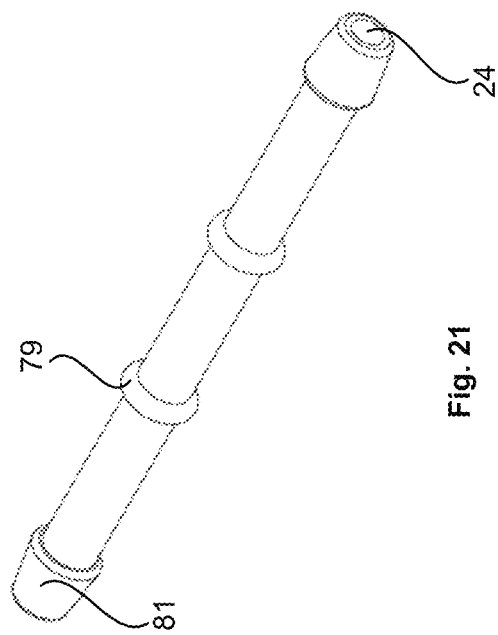
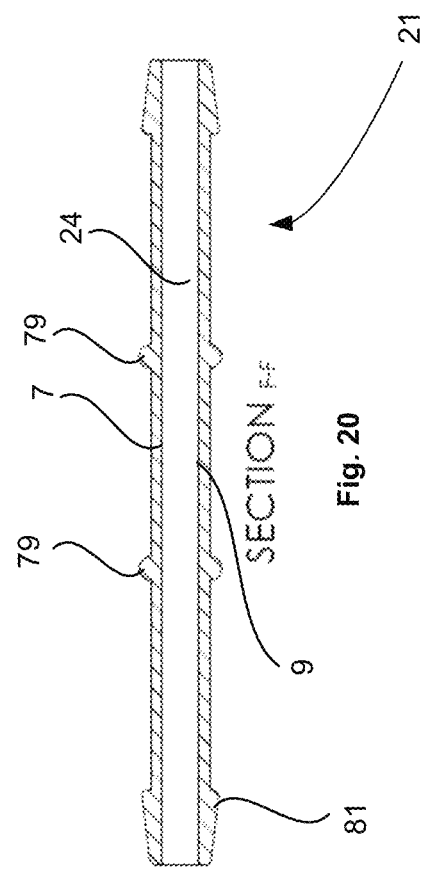
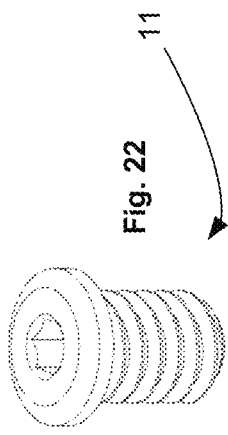
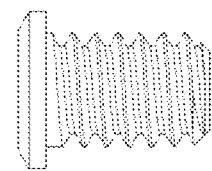

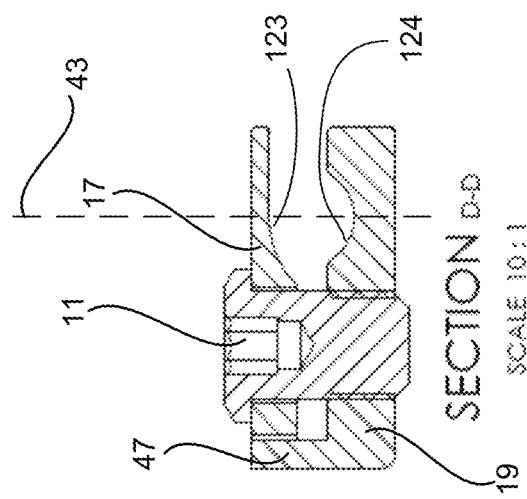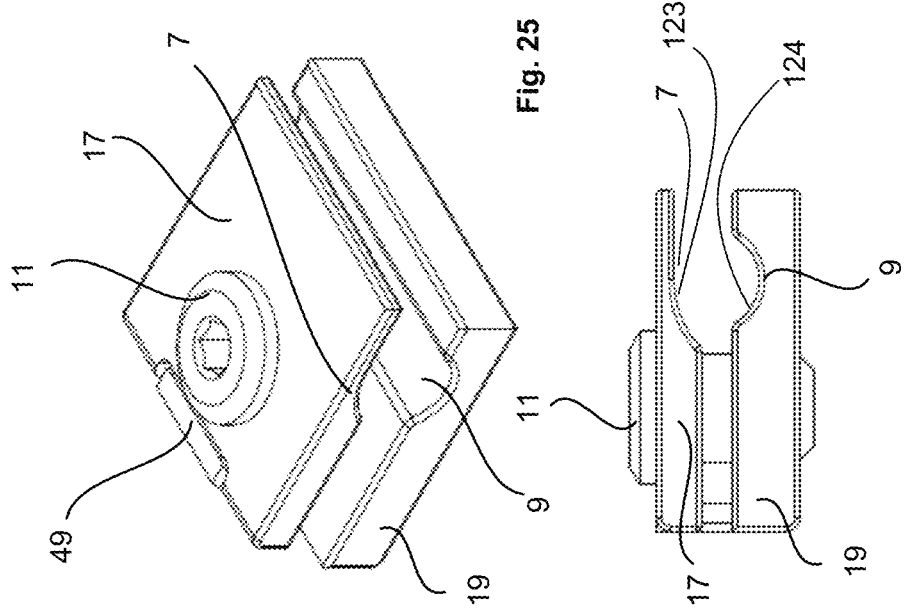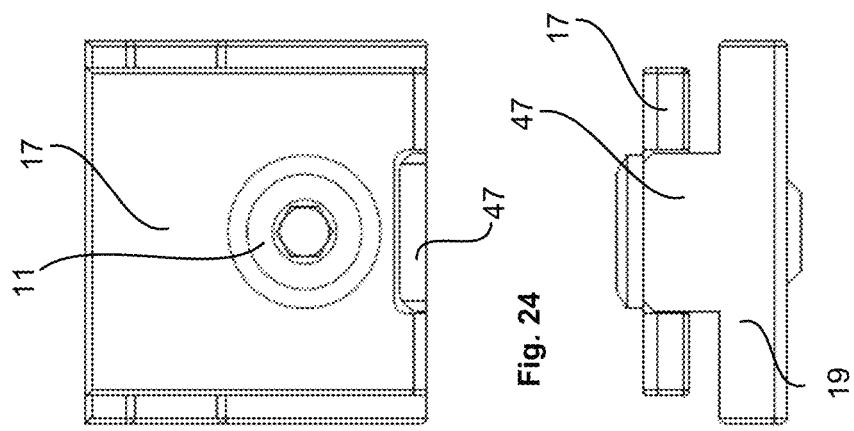

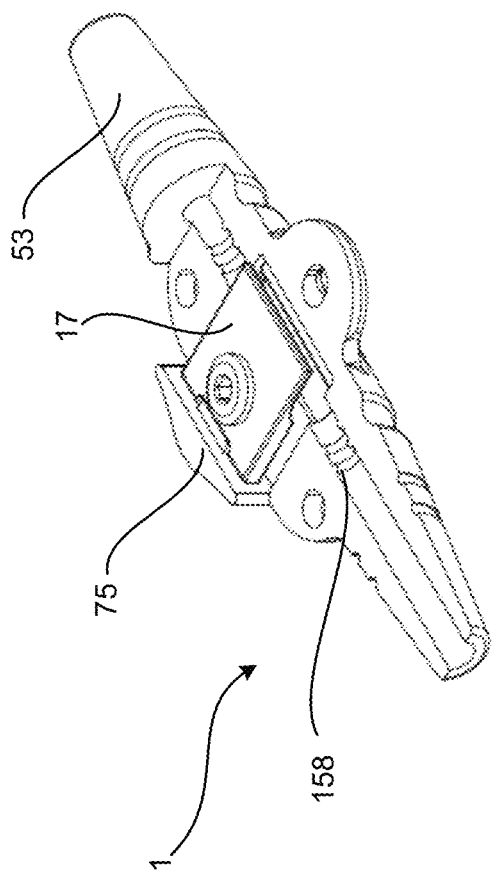
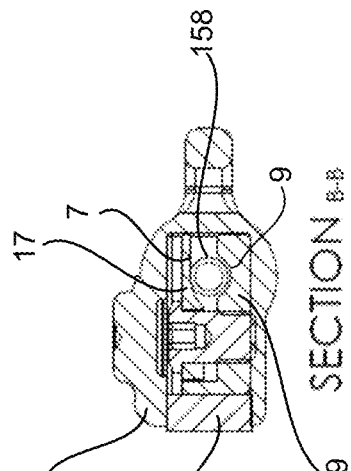
Fig. 30
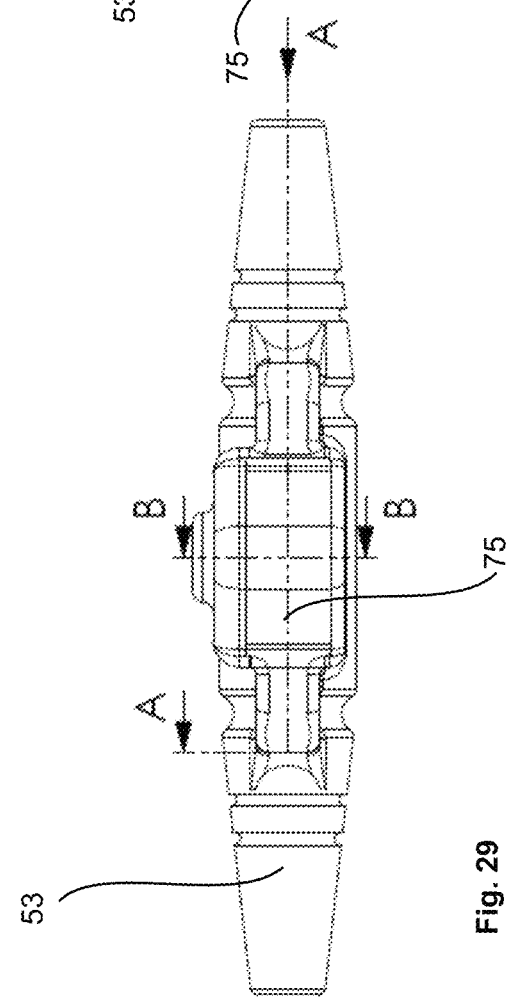
Fig. 31
Fig. 29

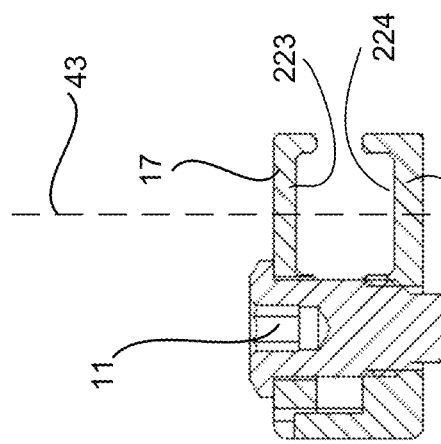
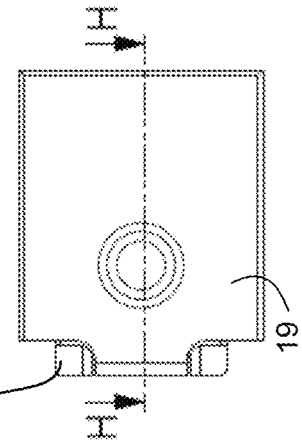
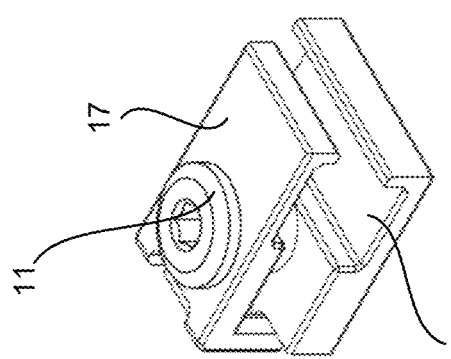
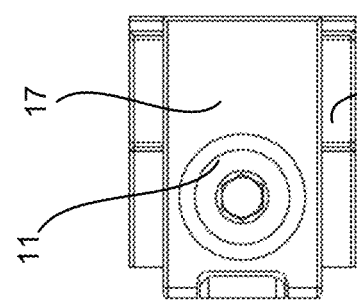
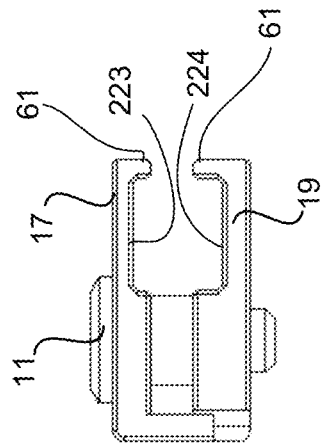
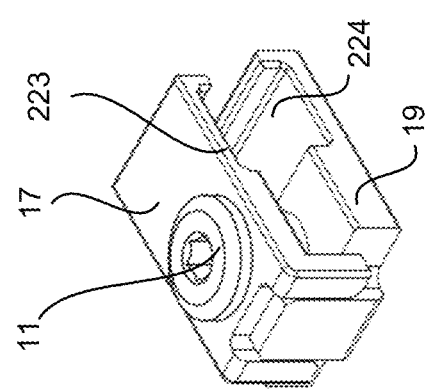
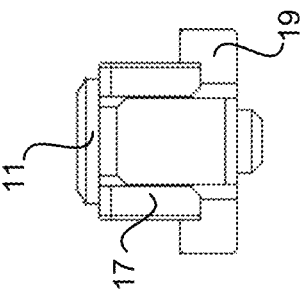

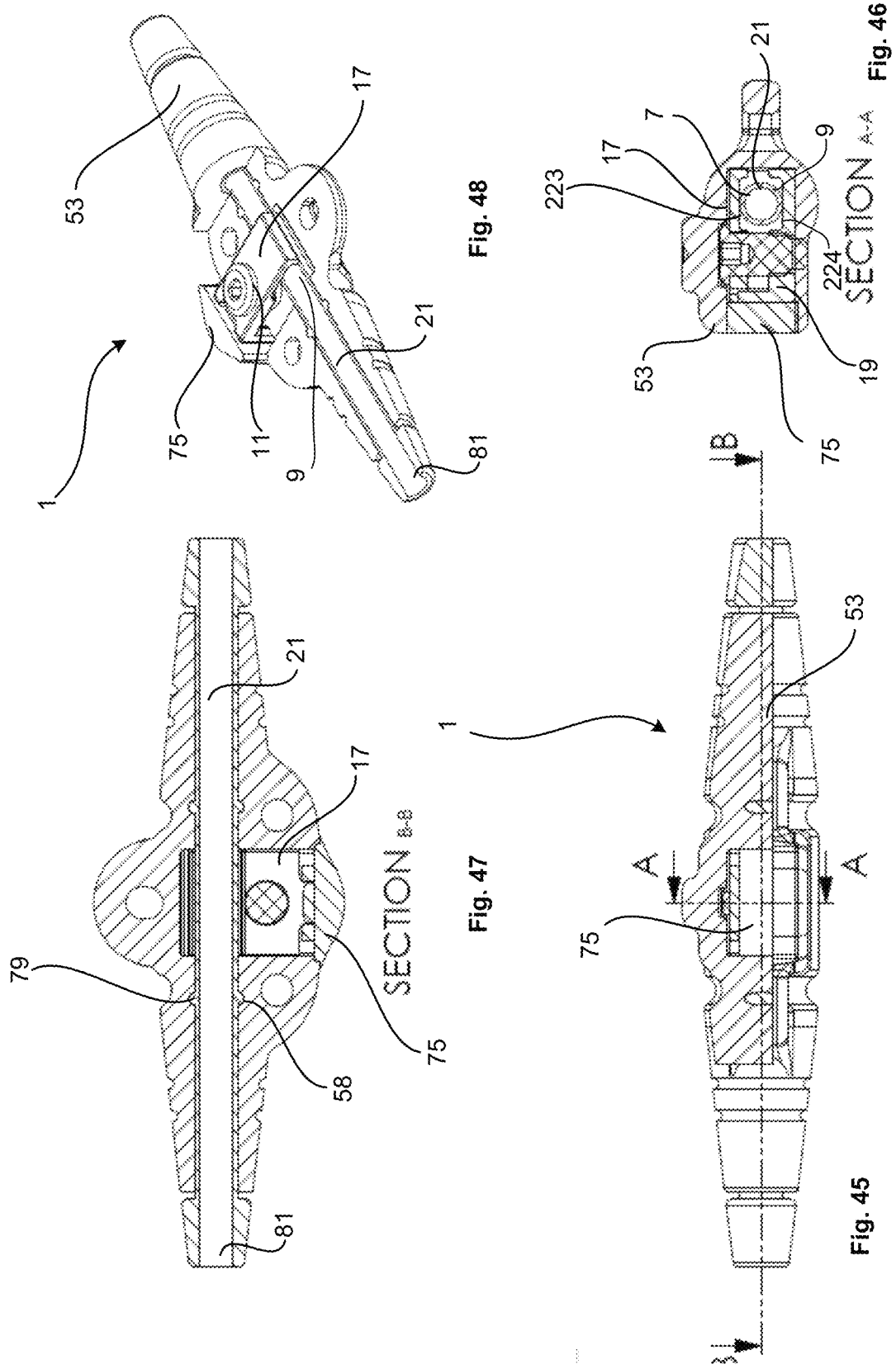

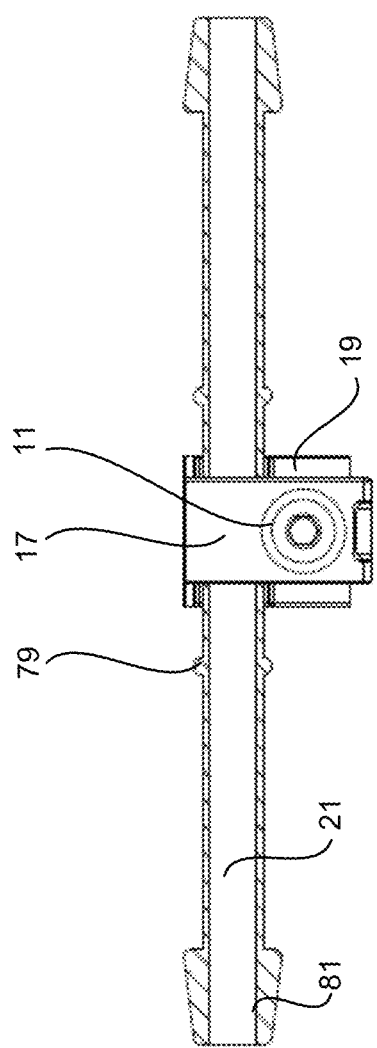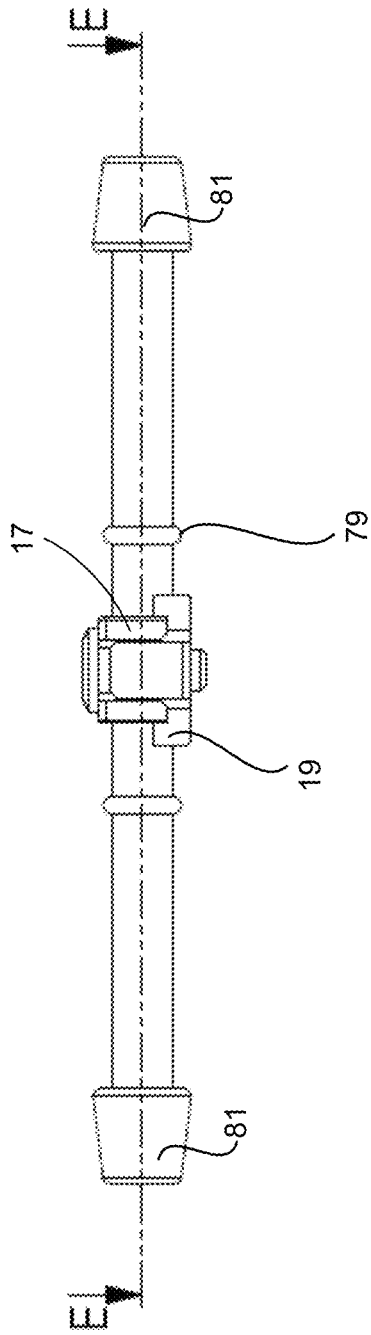

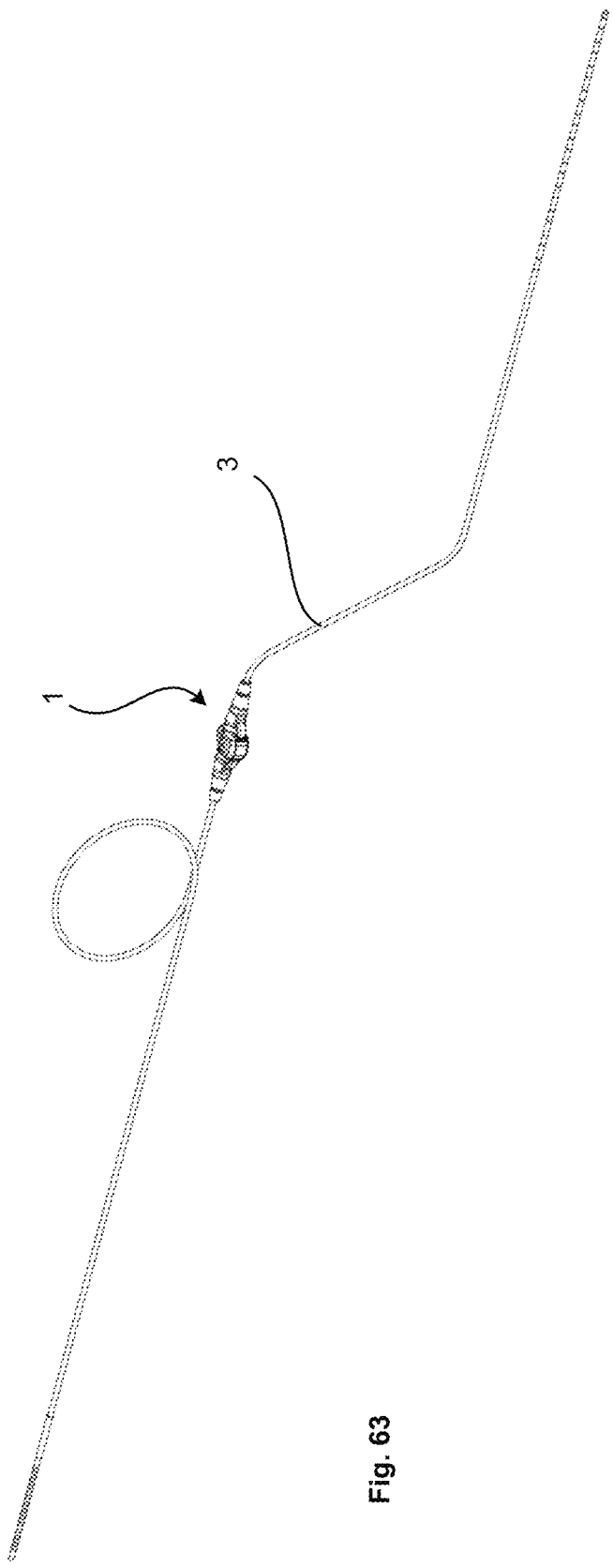
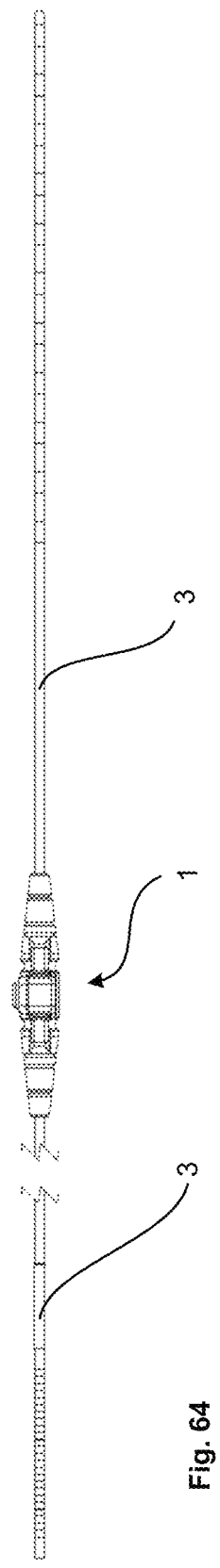
Fig. 63
Fig. 64

LEAD ANCHOR

TECHNICAL FIELD

The present disclosure relates to a lead anchor to secure a lead in tissue of a patient. This can include securing leads for spinal cord stimulation or cerebral palsy treatment.

BACKGROUND

Stimulation leads for pain management or other medical treatments are operatively positioned in patients to deliver therapy. The location of the leads is important to deliver the desired effect and one technique includes using lead anchors to secure the stimulation leads to the tissue of the patient. This includes lead anchors that grasp the lead. Known lead anchors can exert high levels of compressive force on the leads thereby causing the compression of the central lumen of the lead. Such a high level of compressive force, and prolonged stress, can result in fractures in the lead whilst in situ in the patient.

Due to the compression of the central lumen, and potential damage, the position of the lead is difficult to adjust within the body of the patient if such a need arises. In a specific example, the leads inserted in children would desirably need regular adjustments due to the growth of the bones and tissue. In such cases, it is preferable to insert a stylet into the central lumen of the lead and adjust the position of the leads. This can be difficult, or impeded, if the lead anchor has caused the central lumen of the lead to close or collapse due to the compressive force.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

It is desirable to have a lead anchor that imparts adequate levels of force to retain the lead whilst avoiding, or reducing, compression of a lead lumen within the lead.

A lead anchor to secure a stimulation lead with an internal lead lumen, the lead anchor comprising: a first clamp surface; a second clamp surface opposed to the first clamp surface; and an adjustable fastener to selectively draw the first clamp surface towards the second clamp surface to secure the stimulation lead located between the first clamp surface and the second clamp surface, wherein the first clamp surface and the second clamp surface are profiled to apply clamping force to secure the stimulation lead while maintaining an open internal lead lumen.

In some examples, the lead anchor further comprises: a first clamping element associated with the first clamp surface; and a second clamping element associated with the second clamp surface, wherein the adjustable fastener is configured to selectively move the first clamping element relative to the second clamping element.

In some examples of the lead anchor, the first clamp surface is on the first clamping element and the second clamp surface is on the second clamping element.

In some examples of the lead anchor, the first clamping element is slidingly engaged with the second clamping element to: (i) enable relative movement of the first clamp surface towards the second clamp surface along a clamping axis; and (ii) restrict relative movement of the first clamp surface and the second clamp surface around the clamping axis.

In further examples of the lead anchor, the first clamping element is slidingly engaged to the second clamping element with a tongue and groove.

In further examples of the lead anchor, the adjustable fastener selectively draws the first clamping element to the second clamping element along a fastener axis that is substantially parallel to the clamping axis, and wherein the fastener axis does not pass through the first clamp surface nor the second clamp surface.

In some examples, the lead anchor further comprises: an interior sleeve, wherein at least one of the first clamp surface and the second clamp surface is on the interior sleeve, and wherein at least part of the interior sleeve is secured between the stimulation lead and the first clamping element and/or the second clamping element.

In further examples of the lead anchor, the interior sleeve comprises a tubular member having both the first clamp surface and the second clamp surface.

In some examples of the lead anchor, at least one of the first clamping element and the second clamping element includes an arcuate concave surface.

In some examples of the lead anchor, the first clamp surface and/or the second clamp surface comprises an arcuate concave cross section to receive an outer surface of the stimulation lead.

In further examples of the lead anchor, the arcuate cross section has a radius of curvature corresponding to a radius of curvature of the outer surface of the stimulation lead.

In further examples of the lead anchor, the arcuate cross section has a radius of curvature greater than a radius of curvature of the internal lead lumen of the stimulation lead.

In some examples of the lead anchor, the first clamp surface and/or the second clamp surface comprises a V-shaped cross section to receive an outer surface of the stimulation lead.

In some examples of the lead anchor, the adjustable fastener includes a threaded fastener.

In some examples of the lead anchor, the first clamp surface and/or the second clamp surface includes a ribbed surface to aid grip to the stimulation lead.

In some examples, the lead anchor further comprises at least one ramp or chamfer leading to the first clamp surface and second clamp surface to assist insertion of the stimulation lead between the first clamp surface and the second clamp surface before the adjustable faster selectively draws the first clamp surface to the second clamp surface.

In some examples, the lead anchor further comprises an exterior sleeve to house the first clamp surface, second clamp surface, and adjustable fastener, wherein the exterior sleeve includes a plurality of apertures for the stimulation lead to pass through.

In further examples of the lead anchor, the exterior sleeve captures the first clamp surface, second clamp surface, and the adjustable fastener.

In further examples of the lead anchor, the exterior sleeve further comprises suture loops to fix the lead anchor to tissue of a patient.

In further examples of the lead anchor, the exterior sleeve further includes one or more grooves or protrusions to engage with, and retain, the interior sleeve.

In further examples of the lead anchor, the exterior sleeve and the interior sleeve are part of a single common component.

In some examples, the lead anchor further comprises one or more stops to maintain the first clamping surface and the second clamping surface at a specified minimum distance.

BRIEF DESCRIPTION OF DRAWINGS

FIG. 1 illustrates a top view of clamping elements and an adjustable fastener for a lead anchor in accordance with a first example;

FIG. 2 is a perspective view of the clamping elements and adjustable fastener of FIG. 1;

FIG. 3 is an alternative perspective view of the clamping elements and adjustable fastener of FIG. 1;

FIG. 4 is an end view of the clamping elements and adjustable fastener of FIG. 1;

FIG. 5 is a side view of the clamping elements and adjustable fastener of FIG. 1;

FIG. 6 is a sectioned side view of the clamping elements and adjustable fastener of FIG. 4;

FIG. 11 is a side view of the lead anchor in accordance with the first example of a lead anchor including the exterior sleeve and interior sleeve;

FIG. 12 is a sectioned perspective view of the example in FIG. 11;

FIG. 13 is a sectioned end view of the example in FIG. 11 with a lead inside the lead anchor;

FIG. 20 is a sectioned side view of the interior sleeve in accordance with the first example;

FIG. 21 is a perspective view of the interior sleeve of the example in FIG. 20;

FIG. 22 is a perspective view of an adjustable fastener in accordance with a first example;

FIG. 23 is a side view of the adjustable fastener of the example in FIG. 22;

FIG. 24 a top view of clamping elements and an adjustable fastener for a lead anchor in accordance with a second example;

FIG. 25 is a perspective view of the clamping elements and adjustable fastener of FIG. 24;

FIG. 26 is an end view of the clamping elements and adjustable fastener of FIG. 24;

FIG. 27 is a side view of the clamping elements and adjustable fastener of FIG. 24;

FIG. 28 is a sectioned side view of the clamping elements and adjustable fastener of FIG. 24;

FIG. 29 is a side view of the lead anchor in accordance with the second example of a lead anchor including the exterior sleeve;

FIG. 30 is a sectioned perspective view of the example in FIG. 29;

FIG. 31 is a sectioned end view of the example in FIG. 29;

FIG. 38 a perspective view of clamping elements and an adjustable fastener for a lead anchor in accordance with a third example;

FIG. 39 is a top view of the clamping elements and adjustable faster of FIG. 38;

FIG. 40 is an alternative perspective view of the clamping elements and adjustable fastener of FIG. 38;

FIG. 41 is an end view of the clamping elements and adjustable fastener of FIG. 38;

FIG. 42 is a side view of the clamping elements and adjustable fastener of FIG. 38;

FIG. 43 is a bottom view of the clamping elements and adjustable fastener of FIG. 38;

FIG. 44 is a sectioned side view of the clamping elements and adjustable fastener of FIG. 38;

FIG. 45 is a side view of the lead anchor in accordance with the third example of a lead anchor including the exterior sleeve and the interior sleeve;

FIG. 46 is a sectioned end view of the third example in FIG. 45;

FIG. 47 is a sectioned bottom view of the third example in FIG. 45;

FIG. 48 is a sectioned perspective view of the example in FIG. 45;

FIG. 49 is a sectioned top view of the clamping elements and adjustable faster of the third example of a lead anchor with an interior sleeve;

FIG. 50 is a side view of the third example in FIG. 49;

FIG. 63 is a perspective view of the lead anchor with a stimulation lead;

FIG. 64 is a side view of the lead anchor of FIG. 63;

DESCRIPTION OF EMBODIMENTS

Overview

With reference to FIGS. 1 to 6, and 59 to 61, the present disclosure provides a lead anchor 1 to secure a stimulation lead 3 with an internal lumen 5. This includes a stimulation lead for spinal cord stimulation (SCS) or cerebral palsy (CP) treatment applications. FIGS. 63 and 64 illustrate the stimulation lead 3 passing through the lead anchor 1.

Figure 61:
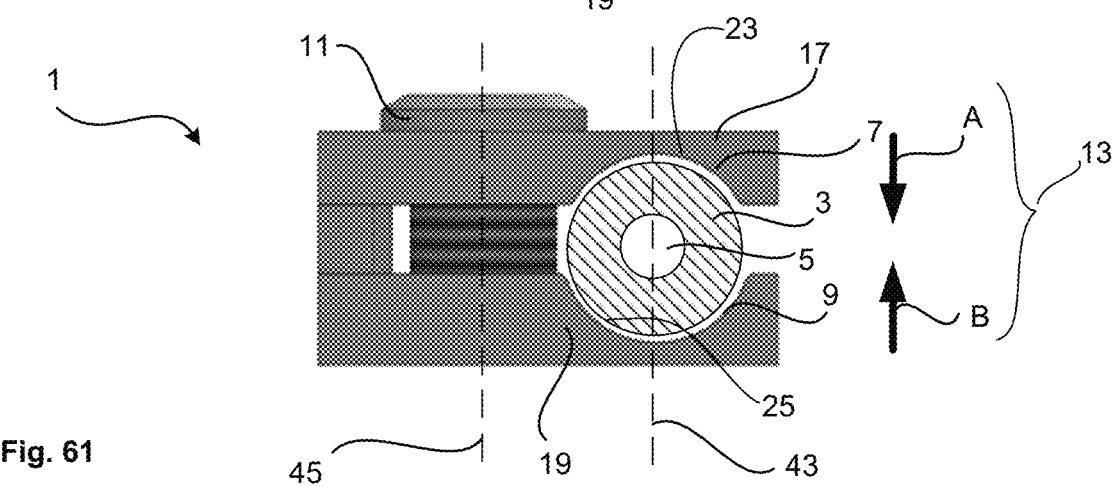
FIG. 61 is a side view of the example of FIG. 59.

The lead anchor 1 includes a first clamp surface 7 opposed to a second clamp surface 9 to receive the stimulation lead 3 in between. An adjustable fastener 11 allows the first clamp surface 7 to be selectively drawn towards the second clamp surface to secure the stimulation lead 3 located between the clamp surfaces 7, 9. The first clamp surface 7 and the second clamp surface 9 are profiled to apply clamping force 13 (in directions A, B as illustrated in FIGS. 5 and 61) to secure the stimulation lead 3 while maintaining an open internal lead lumen 5 (as illustrated in FIGS. 13 and 61).

An advantage of maintaining an open lead lumen 5 is to prevent, or reduce the likelihood, of damage to the stimulation lead 3. Furthermore, having an open lead lumen in the stimulation lead 3 is to allow a stylet to be inserted, or re-inserted, into the lead lumen 5. The stylet is then used by a surgeon to aide positioning the stimulation lead 3. Typically, the stylet is rigid, or semi rigid, and is inserted into a centrally located lead lumen 5 in the stimulation lead 3.

Allowing re-insertion of a stylet into the lead lumen 5 can be particularly advantageous where adjustment of the lead 3 is required, such as for patients that are children who have growing tissue and bones.

First Example—Concave Clamping Elements and Interior Sleeve

A first example of the lead anchor 1 with clamping elements 7, 9 having a concave cross section 23 and interior sleeve 21 will now be described with reference to FIGS. 1 to 23.

Figure 14:
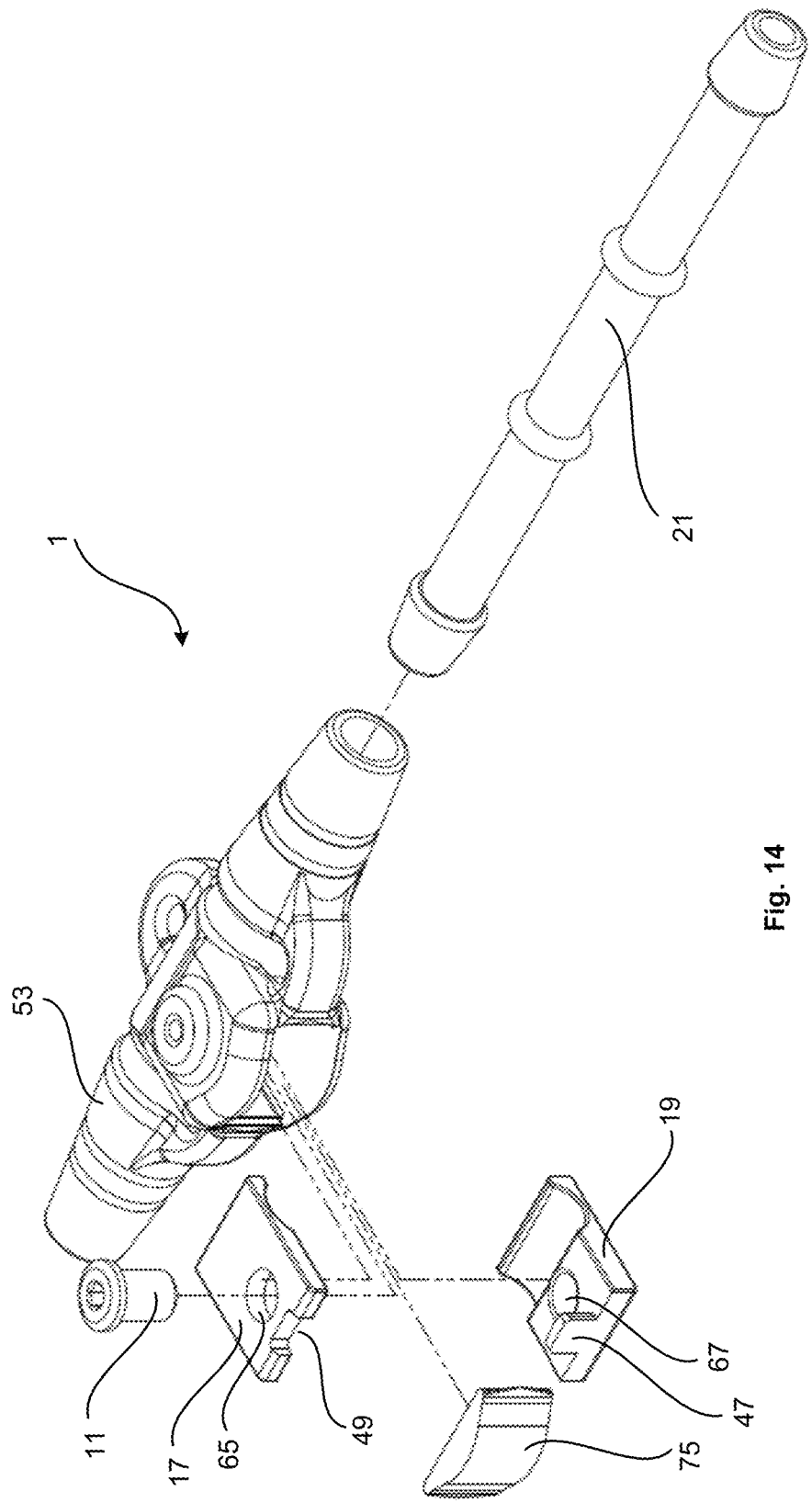
FIG. 14 is an exploded perspective view of the lead anchor in accordance with the first example.

Referring to FIG. 14, the lead anchor 1 includes five major components, including a first clamping element 17, second clamping element 19, an adjustable fastener 11, an interior sleeve 21, and an exterior sleeve 53.

The first clamping element 17 is associated with the first clamp surface 7 and the second clamping element 19 is associated with the second clamp surface 9. In this example, the first and second clamping elements 17, 19 are configured to clamp the interior sleeve 21 (which in turn forms the first and second clamp surfaces 7, 9 acting on the stimulation lead 3). Other examples where the clamping elements 17, 19 having the clamp surfaces 7, 9 acting directly to clamp the stimulation lead 3 will be described in other sections below.

Referring to FIGS. 1 to 6, the first and second clamping elements 17, 19 have respective arcuate concave surfaces 23 that face each other to receive the interior sleeve 21. The arcuate concave surfaces 23 have a radius of curvature greater that the radius of curvature of the internal lead lumen 5 of the stimulation lead 3. In further examples, the arcuate concave surfaces 23 have a radius of curvature greater than the radius of curvature of the outer surface 25 of the stimulation lead 3. The radius of curvature can assist in applying a clamping force necessary to retain the interior sleeve 21 and the stimulation lead 3 whilst ensuring the internal lumen 5 is not inadvertently crushed. In this example the first and second clamping elements 17, 19 apply clamping pressure on the interior sleeve 21 (that has the clamping surfaces 7, 9). However, in examples and configurations where an interior sleeve 21 is not used, the clamping surfaces 7, 9 are on the clamping elements 17, 19 (such as the arcuate concave surfaces 23 that can function as the clamping surfaces 7', 9' in FIGS. 1 to 6).

Referring to FIG. 6, the shape of the arcuate concave surfaces 23,23' of the first and second clamping elements 17, 19 can be different. In this example, the concave surface 23 of the first clamping element 17 has a greater radius that the concave surface 23' of the second clamping element 19. The larger concave surface 23' of the second clamping element 19 may assist in initial centering of the interior sleeve 21. Having a larger curvature on the top concave surface 23 allows for easier deformation of the sleeve which in turn allows for better transfer of clamping force from the element 17 through the interior sleeve 21 to the clamping surface 7 (as there is less wasted force used to compress the sleeve.

The first and second clamping elements 17, 19 further include chamfers 51 (or ramps) that lead to the arcuate concave surfaces 23. This can assist insertion of the stimulation lead 3 between the first and second clamp surfaces before the adjustable fastener 11 draws the clamp surfaces 7, 9 together. This may be particularly advantageous in alternative examples (without the interior sleeve 21) where the chamfers 51 lead to the first and second clamp surfaces 7, 9 that are directly on the first and second clamping elements 17, 19.

Turning to FIGS. 1 to 6, the adjustable fastener 11 is configured to selectively move the first and second clamping element 17, 19 relative to each other. Furthermore, the first and second clamping elements 17, 19 are slidingly engaged 41 with each other. This sliding engagement 41 enables relative movement of the clamping elements 17, 19 (and hence the clamping surfaces 7, 9) along the clamping axis 43 (as shown in FIG. 5). In particular, enabling the first clamping surface 7 to move towards the second clamping surface 9 along the clamping axis 43.

Furthermore, the sliding engagement 41 restricts (and preferably prevents) relative movement of the first clamp surface 7 and the second clamp surface 9 around the clamping axis 43 (i.e. to prevent relative rotation around the clamping axis 43. This ensures the profile of the first and second clamping surfaces 7, 9 remain aligned to clamp the exterior of the stimulation lead 3.

The sliding engagement 41 can include a tongue 47 and groove 49 configuration as illustrated in FIG. 2. It is to be appreciated that other sliding engagement configurations can be used such a T-slot and respective T-shaped projection, dovetail arrangement, key and slot arrangement, etc. As illustrated in FIG. 4. The tongue 47 can be bevelled 48 to assist in insertion into the groove 49.

The adjustable fastener 11 selectively draws the first clamping element 17 to the second clamping element along a fastener axis 45 that is substantially parallel to the clamping axis 43 as illustrated in FIG. 5. The fastener axis 45 does not pass through the first clamp surface nor the second clamp surface 9. Thus the fastener 11 does not act directly above (or below) the stimulation lead 3, which may reduce the likelihood of excessive force that can crush the lead lumen 5. In this example, the adjustable fastener 11 is a threaded fastener (as shown in FIGS. 22 and 23) that is rotated around the fastener axis 45 to selectively adjust the fastener 11. In this particular example, the adjustable fastener 11 passes through an aperture 65 in the first clamping element 17 and engages a threaded aperture 67 in the second clamping element 19.

In some examples, the point(s) at which the fastener acts on the clamping elements 17, 19 is not the same as the axis of the fastener as the clamping elements may not always be parallel. That is, the point of contact is at the edge of the screws head of the fastener 11. This will be discussed later in the sixth example (with reference to FIGS. 65 and 66).

The lead anchor 1 also comprises one or more stops 61 to maintain the first and second clamping surfaces 7, 9 at a specified minimum distance. Referring to FIG. 6, the stops 61 may be surfaces on the first and second clamping elements 17, 19 that abut each other as the adjustable fastener 11 is tightened. By stopping the first and second clamping elements 17, 19 at the specified minimum distance, this can prevent over-tightening and crushing of the stimulation lead 3 whilst providing necessary clamping force to hold the lead 3 in place.

The exterior sleeve 53 will now be described with reference to FIGS. 16 to 19. The exterior sleeve 53 is configured to house parts of the lead anchor 1, including the first clamp surface 7 and the second clamp surface 9 and the adjustable fastener 11. The exterior sleeve 53 includes a plurality of apertures 55, 57 for the stimulation lead 3 to pass through the exterior sleeve 53 and between the first and second clamp surfaces 7, 9.

In this example, the exterior sleeve 53 captively houses the first and second clamping elements 17, 19 and adjustable fastener 11 in a pocket 71. The exterior sleeve 53 includes an access aperture 73 to allow a tool to access the adjustable fastener 11 so that the adjustable fastener 11 can be adjusted whilst inside the pocket 71. The pocket 71 can be closed off by a door 75 to stop, or hinder, contaminants from moving into the pocket 75.

Figures 16, 18:
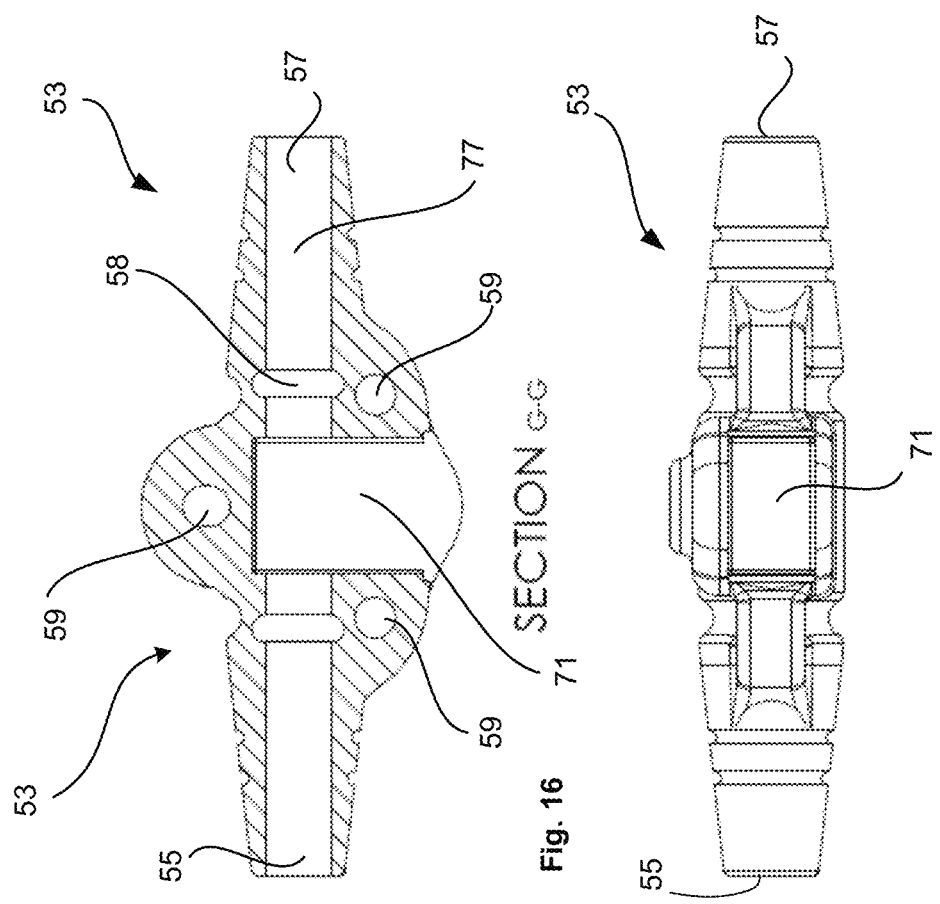
FIG. 16 is a sectioned top view of an exterior sleeve for a lead anchor in accordance with the first example.
FIG. 18 is a side view of the exterior sleeve of the example in FIG. 16.

Turning to FIG. 16, the exterior sleeve 53 includes an internal passage 77 that passes between the apertures 55, 57. The internal passage 77 enables the stimulation lead 3 to pass through the exterior sleeve 53. In this example, the lead 3 passes through the internal sleeve 21 and the internal passage 77 allows for placement of the internal sleeve 21. The internal passage 77 also enables the interior sleeve 21 to be received, at least in part, in the exterior sleeve 53 as illustrated in the partial cross section in FIG. 12. The exterior sleeve 53 includes one or more annular grooves 58 in the internal passage 77 to engage with corresponding annular ribs 79 of the interior sleeve 21. This prevents, or reduces, the likelihood of the interior sleeve 21 slipping out of the internal passage 77 when the lead anchor 1 is assembled with the stimulation lead 3. This may also help to control the thickness of the interior sleeve wall that is in contact with the clamping element 17, 19. This locates the interior sleeve 21 so that it is neither stretched out and thinner or compressed and thicker, which can change the efficacy of the clamp mechanism.

The lead anchor 1 also includes one or more suture loops 59 to fix the lead anchor 1 to tissue of a patient. The suture loops 59 enable a surgeon to attach sutures, or other biocompatible fasteners, to tissue (including bone) of a patient. In further example, the suture loops 59 may enable the surgeon to attach or otherwise fix the lead anchor 1 to another anchor point. The attachment of the lead anchor 1, in turn, secures the stimulation lead 3.

FIGS. 20 and 21 illustrate an example of the interior sleeve 21. The interior sleeve 21 includes a tubular member wherein the tubular internal surface forms both the first and second clamp surfaces 7, 9. Since the internal surface is tubular, the first and second internal surfaces have an arcuate concave cross section 24. In preferred examples, the arcuate concave cross section has a radius of curvature that corresponds to the radius of curvature of the outer surface 25 of the stimulation leads 3. The first and second clamp surfaces 7, 9 receive clamping pressure from the first and second clamping elements 17, 19 to hold the stimulation lead 3.

The interior sleeve 21 further includes annular ribs 79 at an external facing surface. The annular ribs 79 engage with corresponding annular grooves 58 to resist relative movement of the interior sleeve 21 out of the passage 77 of the exterior sleeve 53. The ends of the interior sleeve 21 also include enlarged heads 81 that abuts the edges of the apertures 55, 57 of the exterior sleeve 53 to further retain the interior sleeve 21 with the exterior sleeve 53.

Figure 15:
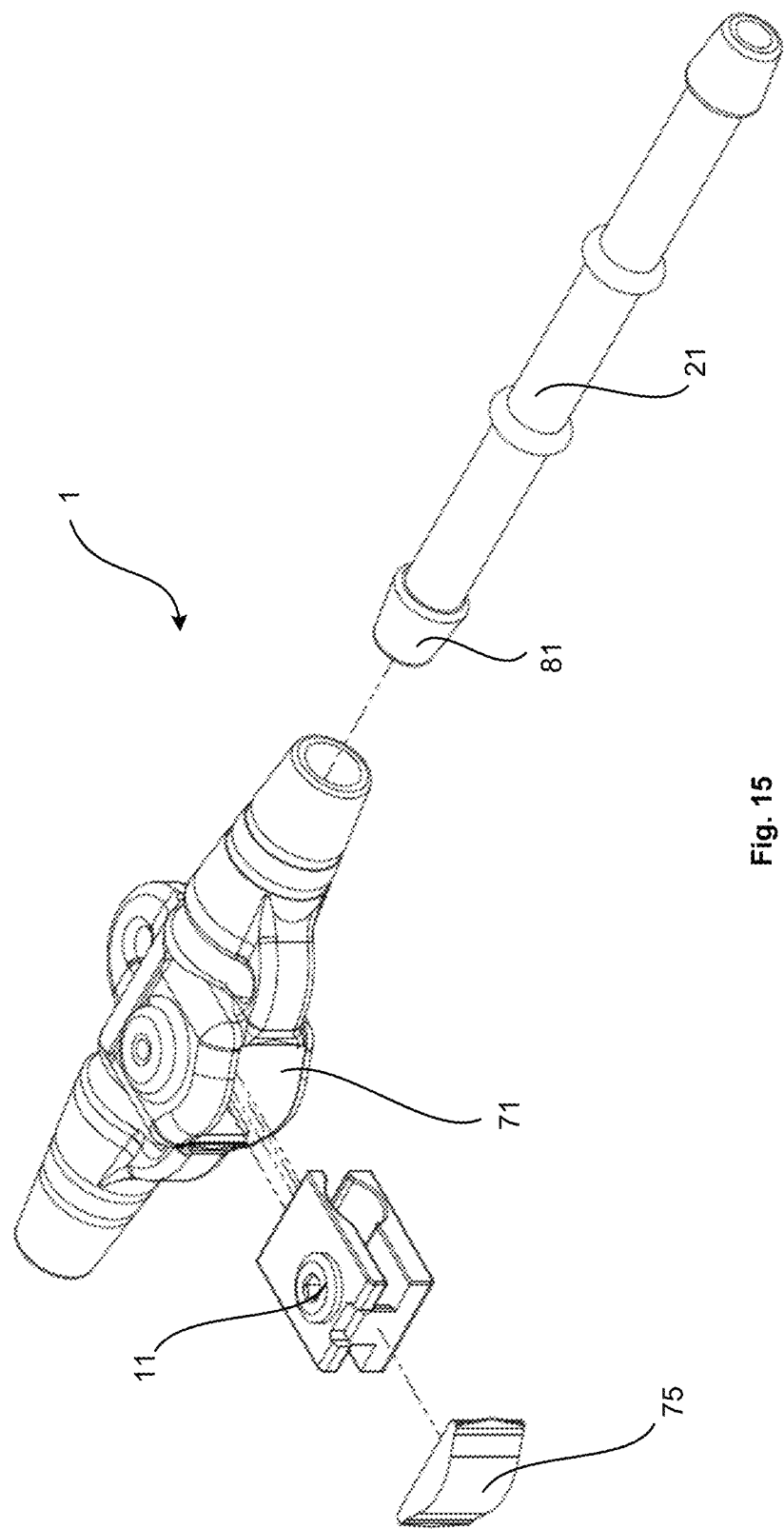
FIG. 15 is a perspective view of a partially assembled lead anchor of the first example in FIG. 14.
Figures 17, 19:
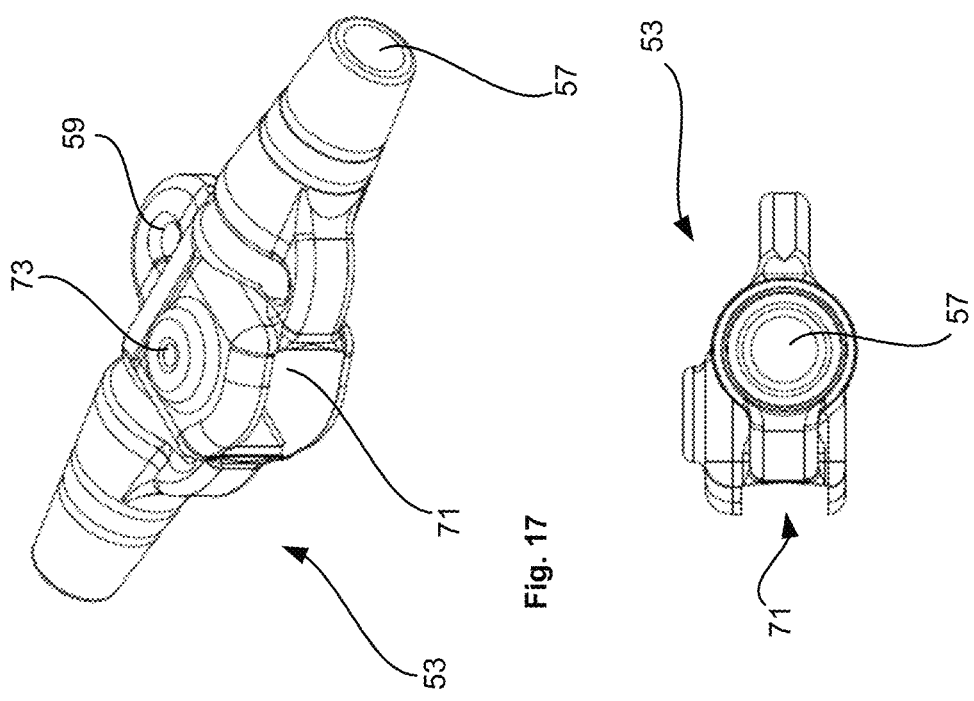
FIG. 17 is a perspective view of the exterior sleeve of the example in FIG. 16.
FIG. 19 is an end view of the exterior sleeve of the example in FIG. 16.

Method of assembling will now be described with reference to FIGS. 7 to 16. In FIG. 14, the components of the lead anchor 1 are shown in exploded view. The first clamping element 17 and second clamping element 19 are joined by sliding the tongue 47 into the groove 49 and assembled together by screwing in the adjustable fastener 11. Once this sub-assembly is assembled, as illustrated in FIG. 15, the clamping elements 17, 19 are inserted into the pocket 71 of the exterior sleeve 53. The door 75 can be located to cover the pocket 71 and to protect the components therein. The interior sleeve 21 is then inserted through the internal passage 77 of the exterior sleeve 53. Since the interior sleeve 21 is resilient and hollow, the interior sleeve 21 can deform to a smaller shape of parts of the internal passage 77. The tapered head 81 of the interior sleeve 21 assist in insertion through the apertures 55, 57. This results in an assembled lead anchor 1, as illustrated in FIGS. 11 to 13, that is ready for use with a stimulation lead 3.

In another example, the method of assembling the lead anchor 1 is achieved by chemically expanding the exterior sleeve 53 and then inserting the interior sleeve 21 into the exterior sleeve 53. The clamping elements 17, 19 are then assembled and inserted through the pocket 71, followed by the door 75 to close the pocket 71. In some examples, the adjustable fastener 11 is engaged after the clamping elements 17, 19 have been inserted into the pocket 71. However in other alternatives, the adjustable fastener 11 can be mated to the clamping elements 17, 19 at other stages such as before insertion in to the pocket 71.

Figure 9:
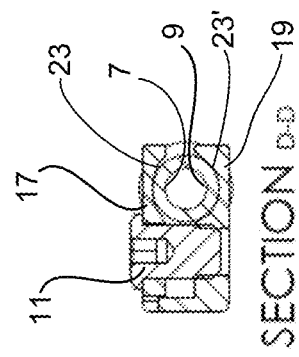
FIG. 9 is a sectioned end view of the example in FIG. 7.
Figure 8:
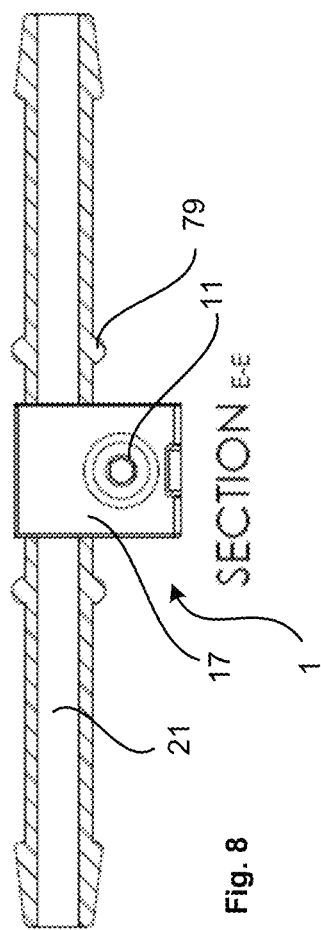
FIG. 8 is a top view of the example in FIG. 7 with a sectioned lumen.
Figure 7:
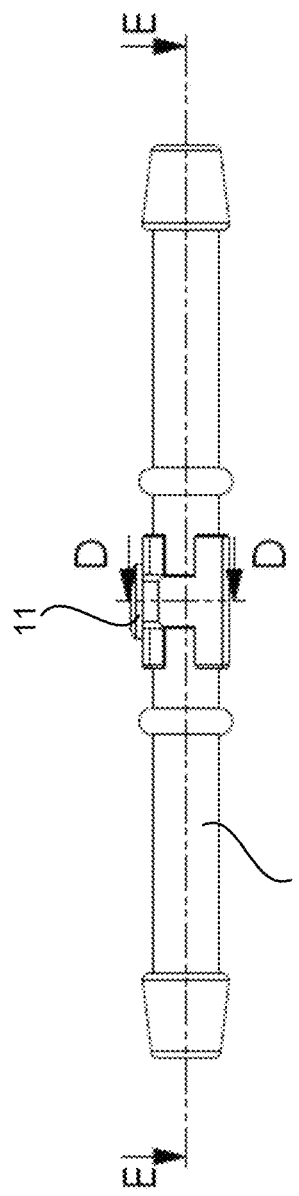
FIG. 7 is a side view of the clamping elements and adjustable faster of the first example of a lead anchor with an interior sleeve.
Figure 10:
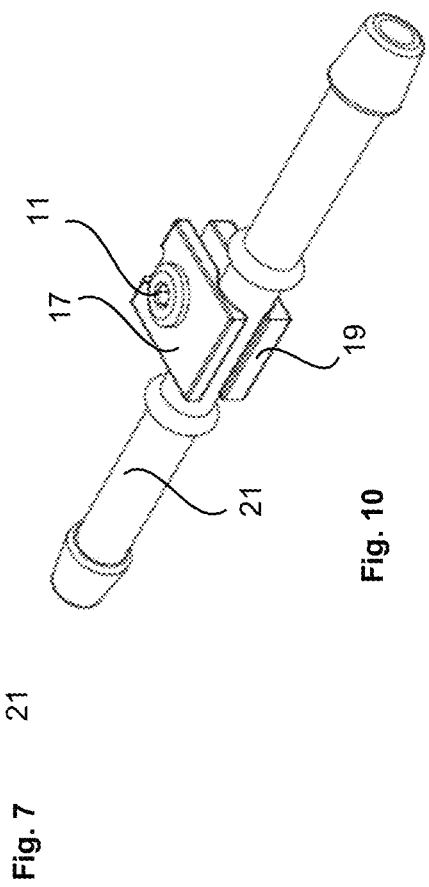
FIG. 10 is a perspective view of the example in FIG. 7.

The stimulation lead 3 is inserted through the hollow tube of the interior sleeve 21. FIGS. 63 and 64 illustrate the assembled lead anchor 1 with the stimulation lead 3. In some examples, the surgeon may use more than one lead anchor for a single stimulation lead to enable anchoring at multiple points. The surgeon can place a stylet through the internal lead lumen 5 to assist locating stimulation lead 3 at a desired location in the patient. The lead anchor 1 can be secured to a location on the stimulation lead 3 by selectively operating the adjustable fastener 11 such that the first clamp surface 7 is drawn towards the second clamp surface 9 to secure the stimulation lead between the clamp surfaces 7, 9. Referring to FIGS. 7 to 9, that shows the lead anchor 1 without the exterior sleeve 53 for better clarity, as the adjustable fastener 11 is tightened, the first and second clamping elements 17, 19 are drawn together. In turn, the arcuate concave surface 23 of the clamping elements 17, 23 apply pressure to the interior sleeve 21. This results in the first and second clamp surfaces 7, 9, that are also arcuate in cross section, clamping towards the lead 3. Since the clamp surfaces 7, 9 are profiled with an arcuate cross section 24, this prevents or reduces excessive force than can crush the lead 3 and the lead lumen 5. In some examples, the clamping pressure is in the range of 10 to 15 newtons. In other examples, the clamping pressure may be greater than 5 newtons.

Referring to FIGS. 11 to 13 showing the assembled lead anchor 1, the surgeon can secure the lead anchor 1 to the tissue of the patient by using the suture loops 59. The stylet is withdrawn from the lead lumen 5.

It is to be appreciated that the steps above may be varied depending on the surgical technique. For example, the surgeon may elect to secure the lead anchor 1 to the tissue of the patient before selectively operating the adjustable fastener 11 to clamp the stimulation lead 3. In other examples, the surgeon may elect to withdraw the stylet from the lead lumen 5 before operating the adjustable fastener 11.

If desired, further procedures may be performed to reposition the location of the lead 3. This may include the surgeon selectively adjusting the fastener 11 to release the lead 3. The lead 3 can be repositioned with (or if desired without) the aid of a stylet inserted in the lead lumen 3. Once the lead is located in the new position, the adjustable fastener 11 is operated to secure the lead 3 in place.

The components of the lead anchor 1 are preferable constructed of biocompatible materials. The first and second clamping elements 17, 19 are made of a rigid material, than can include: stainless steel, titanium alloy, NiCo alloy (nickel cobalt), NiTi alloy (nickel titanium). The rigid material may also include polymers, that includes but not limited to: PEEK (polyether ether ketone) or HDPE (high density polyethylene). The adjustable fastener 11 may be constructed of: stainless steel, titanium alloy, NiCo alloy, NiTi alloy, and/or polymers (such as those discussed above). The exterior sleeve 53 may be constructed of a rigid or semi-rigid, or flexible material. Rigid materials may include: epoxies, and metals (such as Nitinol—an NiTi alloy). Flexible or semi-rigid materials may include silicones and polyurethanes. Importantly, the exterior sleeve 23 is exposed to tissue and is constructed of biocompatible material. The interior sleeve 21 is preferably constructed of a flexible, resilient and elastic material. The interior sleeve 21 is also preferably constructed of biocompatible materials. This allows easy insertion into the exterior sleeve 23, resists permanent distortion to the lead 3, and flexibility for the lead to be inserted. Suitable materials for the interior sleeve 21 can include: silicones and/or polyurethanes. In other examples, the interior sleeve 21 is made of an NiTi alloy that is selected to have good elasticity.

Second Example—Partial Concave Clamp Surface

A second example with partial concave clamp surfaces 7, 9 will now be described with reference to FIGS. 24 to 37. The main difference compared with the first example is that the first clamp surface 7 is on the first clamping element 17 and the second clamp surface 9 is on the second clamping element 19. That is the clamping elements 17, 19 directly clamp onto the stimulation lead 3. Thus no interior sleeve 21 is used in the illustrated configuration of the second example. Furthermore, the first clamp surface 7 in the second example has a different shape profiles 123, 124.

FIGS. 24 to 28 illustrate the clamping elements 17, 19 with an adjustable fastener 11. The first clamping element 17 has a first clamp surface 7 that has a profile 123 comprising a cross section that includes a partially curved portion and a straight portion. The second clamping element 17 has a second clamp surface 9 that has a profile 124 that has a substantially arcuate concave cross section.

The profiles 123, 124 are configured so that when adjustable fastener draws the clamp surface 7 to the second clamp surface 9, sufficient clearance is provided along the clamping axis 43 so that the lead lumen 5 is open and not crushed.

FIGS. 29 to 31 illustrate an assembled lead anchor where the exterior sleeve 53 captures the first clamp surface 7, second clamp surface, and the adjustable fastener 11. This aids holding the components of the lead anchor 1 together.

The exterior sleeve 53 includes annular ribs 158 that can aid holding the lead 3 in place, such as temporarily providing pressure to hold the lead in place whilst (and before) the adjustable fastener 11 is selectively operated to draw the clamp surfaces 7, 9 together. The structure of the exterior sleeve 53, configured to be use without an internal sleeve 21, is illustrated in further detail in FIGS. 34 to 37.

Figure 33:
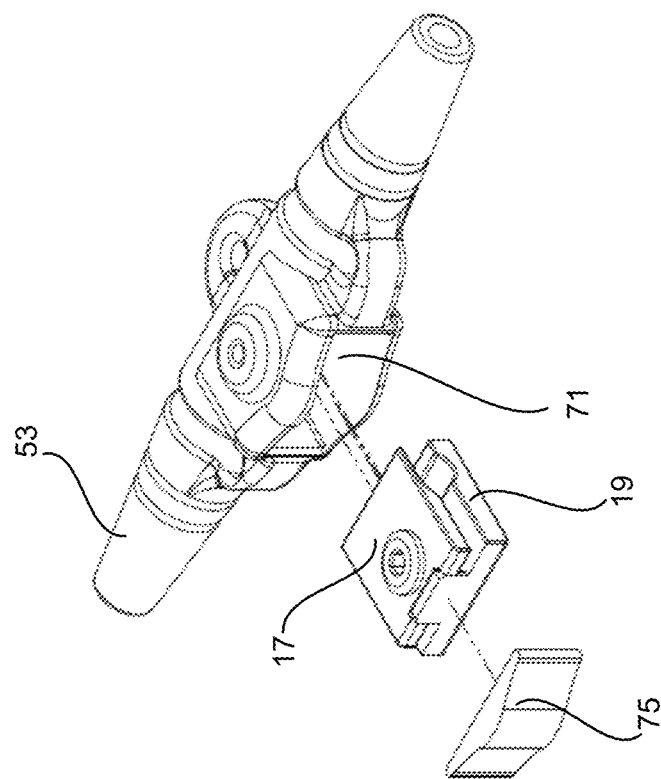
FIG. 33 is a perspective view of a partially assembled lead anchor of the second example in FIG. 32.
Figure 32:
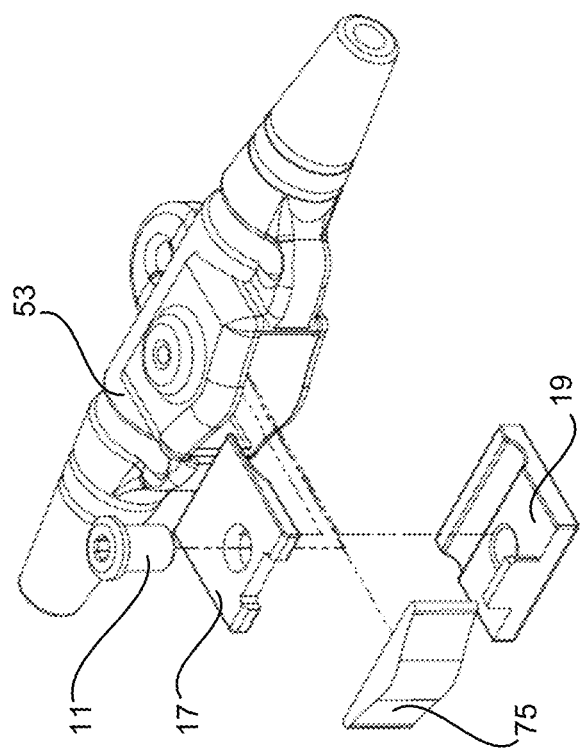
FIG. 32 is an exploded perspective view of the lead anchor in accordance with the second example.
Figure 36:
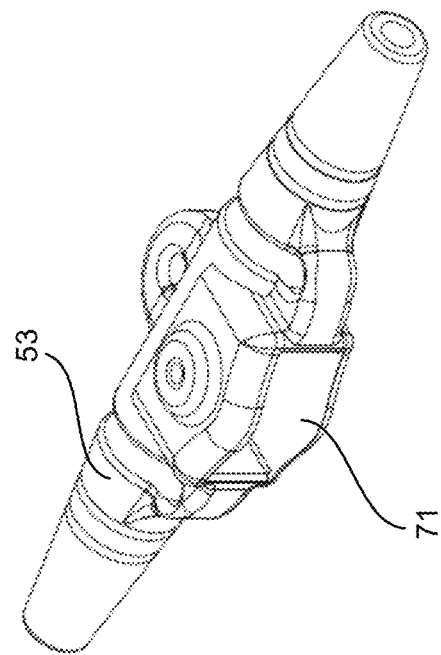
FIG. 36 is a perspective view of the exterior sleeve of the example in FIG. 34.
Figure 37:
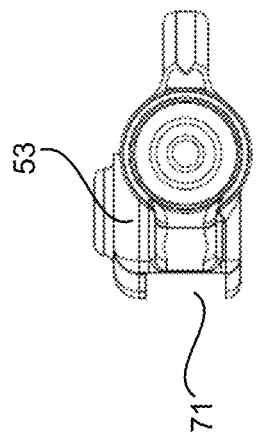
FIG. 37 is an end view of the exterior sleeve of the example in FIG. 34.
Figure 35:
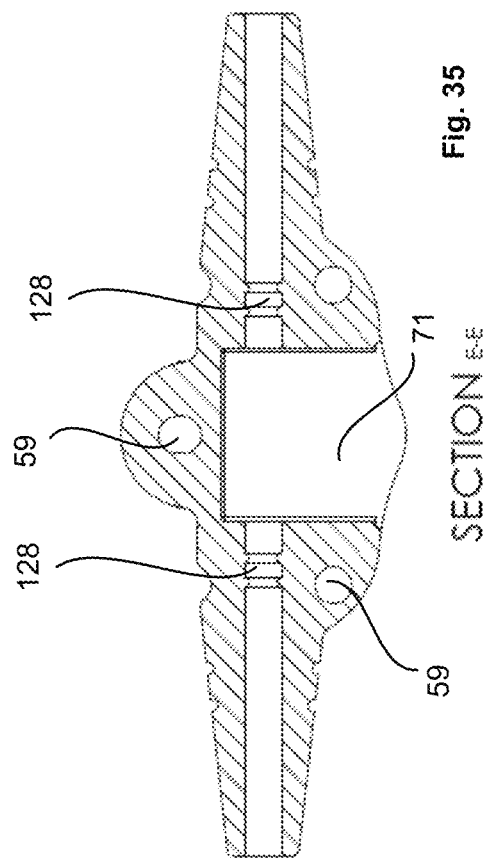
FIG. 35 is a sectioned top view of the exterior sleeve of the example in FIG. 34.
Figure 34:
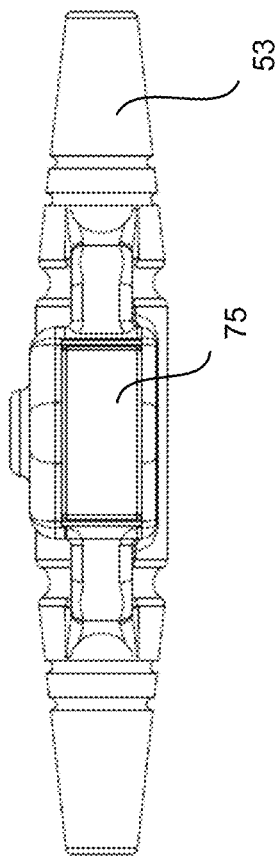
FIG. 34 is a side view of the exterior sleeve for a lead anchor in accordance with the second example.

FIGS. 32 and 33 illustrate a sequence of the lead anchor 1 of the second example in different stages of assembly. It is to be appreciated that the methods of assembly and attachment of the lead anchor 1 to the lead and tissue can include methods as described above.

Third Example—Partially C-Shaped Clamp with Interior Sleeve

A third example with clamp surfaces 7, 9 formed in part by the interior sleeve 21 and partially C-shaped clamps will be described with reference to FIGS. 38 to 52.

The third example is differs, from the first example, in that the first clamping element 17 and the second clamping element 19 have C-shaped profiles 223, 224. Referring to FIGS. 38 to 43, the C-shaped profiles have a substantially flat surface with a pair of opposing lips facing each other. In this example the cross section of the C shaped profile 223, 224, as illustrated in FIG. 44, is substantially the same for the first and second clamping elements 17, 19. However, the depth of the profile, as best illustrated in FIG. 40 shows that the C-shaped profile of the first clamping element 17 is less than, and thus have less surface area, that the C-shaped profile of the second clamping element 19.

The C-shaped profile of the opposing first and second clamping elements 17, 19 prevent the substantially flat surfaces of the profiles from contacting each other. In particular, the flat surfaces of the profiles that the clamping axis 43 passes through as shown in FIG. 44. In some examples, the lips of the C-shaped profiles form stops 61 to maintain a minimum distance of the opposing flat surfaces of the C-shape profiles. In turn, this limits the minimum distance that the clamp surfaces 7, 9 are from each other to prevent crushing of the lead 3 and lead lumen 5.

As illustrated in FIGS. 46 and 49 to 50 the C-shaped profile of the first and second clamping elements 17, 19 clamp against the interior sleeve 21, which is similar to the sleeve in the first example. The clamp surfaces 7, 9 in turn clamp against the lead 3. The interior sleeve 21 may distort within the substantially square channel formed by the C-shaped profiles, but as noted above the stops 61 limit the displacement to prevent crushing of the lead lumen 5.

Figure 51:
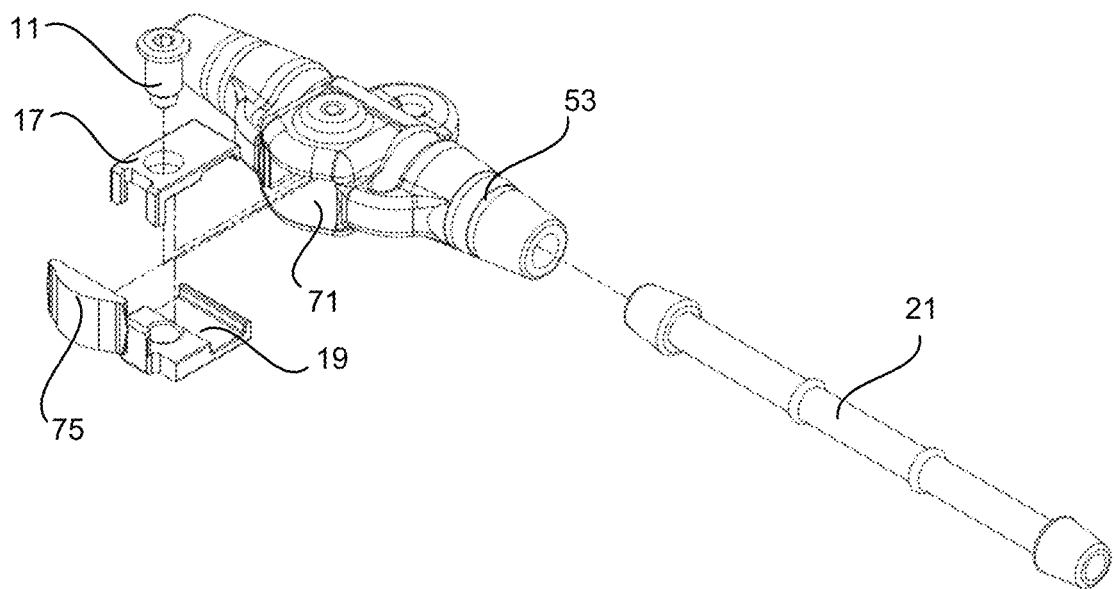
FIG. 51 is an exploded perspective view of the lead anchor in accordance with the third example.
Figure 52:
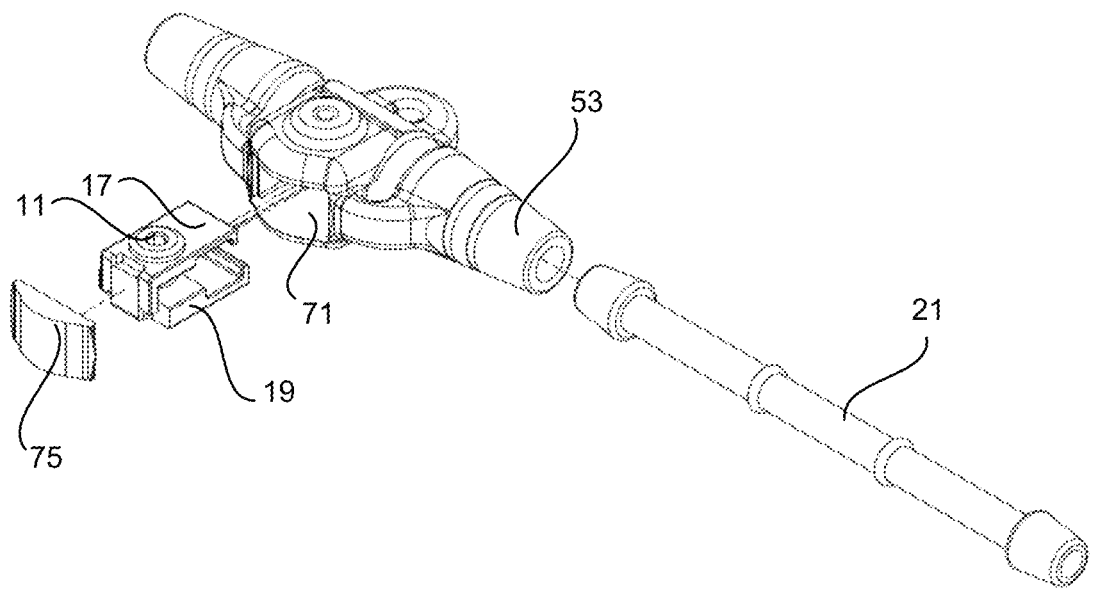
FIG. 52 is a perspective view of a partially assembled lead anchor of the third example in FIG. 51.
Figure 55:
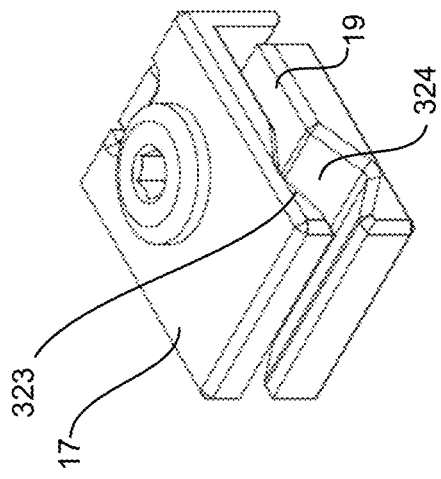
FIG. 55 is an alternative perspective view of the clamping elements and adjustable fastener of FIG. 53.

FIGS. 51 and 52 illustrate a sequence of the lead anchor 1 of the third example in different stages of assembly.

Fourth Example—V-Shaped Clamp

A fourth example with clamp surfaces comprising a V-shaped cross section 323, 324 will be described with reference to FIGS. 53 to 58. In this example, the first and second clamping elements 17 and 19 have corresponding V-shaped profiles 323, 324.

Figure 58:
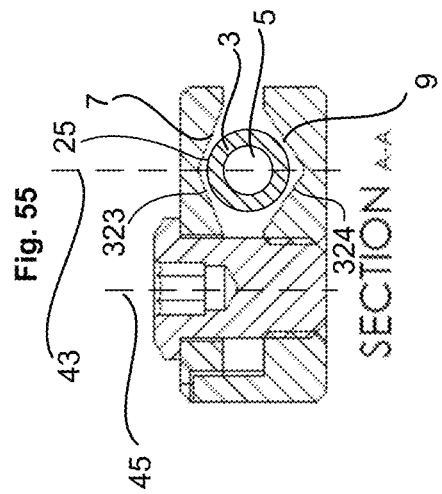
FIG. 58 is a sectioned side view of the clamping elements and adjustable fastener of FIG. 53.
Figure 54:
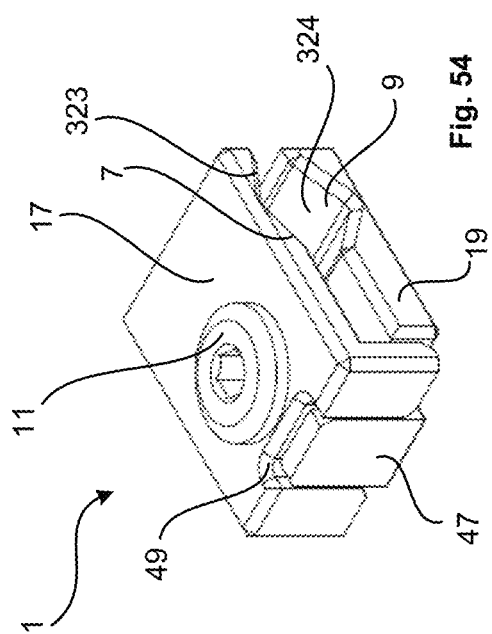
FIG. 54 is a perspective view of the clamping elements and adjustable fastener of FIG. 53.
Figure 57:
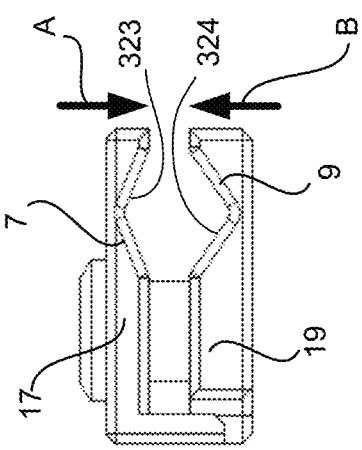
FIG. 57 is a side view of the clamping elements and adjustable fastener of FIG. 53.
Figure 53:
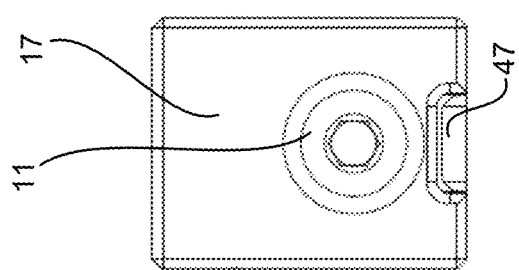
FIG. 53 illustrates a top view of clamping elements and an adjustable fastener for a lead anchor in accordance with a fourth example.
Figure 56:
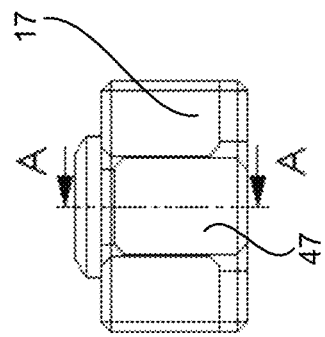
FIG. 56 is an end view of the clamping elements and adjustable fastener of FIG. 53.
Figure 59:
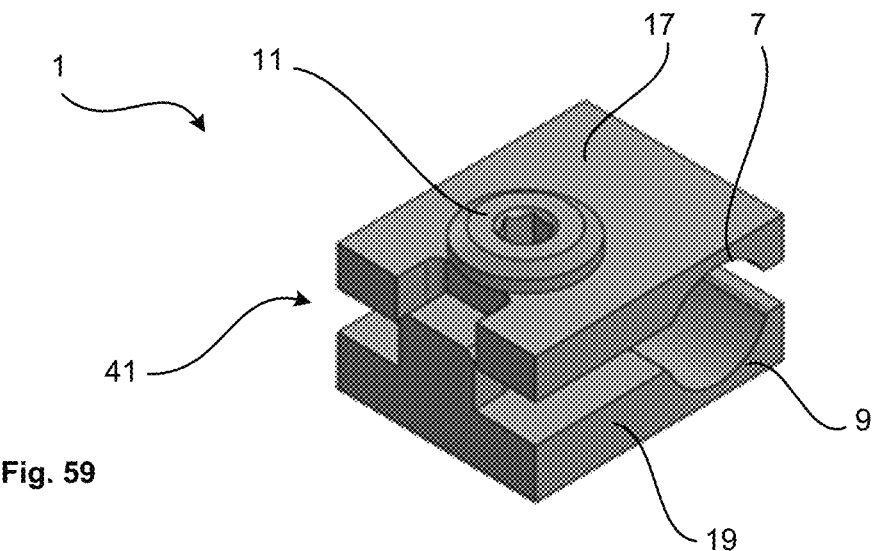
FIG. 59 illustrates a perspective view of clamping elements, including corresponding clamp surfaces, and an adjustable fastener for a lead anchor in accordance with a fifth example.
Figure 60:
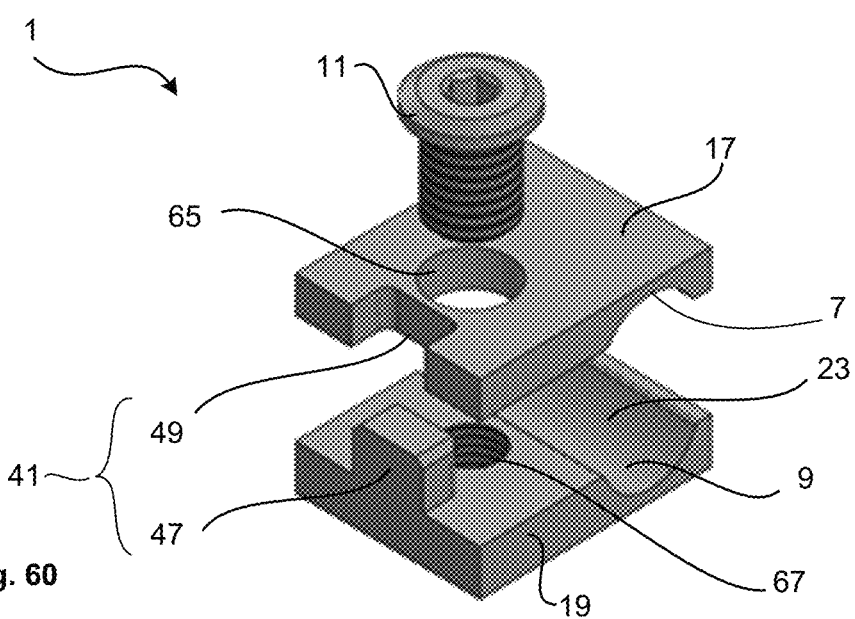
FIG. 60 is an exploded perspective view of the fifth example of FIG. 59.

In some configurations, the V-shaped profiles 323, 324 are the first and second clamp surfaces 7, 9 that directly clamp to the stimulation lead 3. The V-shape 323, 324, prevents, or reduces, clamping force 13 from directly transmitted to the lead 3 along the clamping axis 43 as illustrated in FIG. 58. This prevents, or reduces, the likelihood of the clamping force 13 crushing the lead 3 and lead lumen 5.

In some configurations, the V-shaped profiles 323, 324 are configured to act on an internal sleeve 21 as described in other examples above. The internal sleeve 21, in turn, provide the first and second clamp surfaces. The V-shaped profiles 323, 324 in such a configuration also prevents, or reduces clamping force 13 from directly acting along the clamping axis 43.

It is to be appreciated that the fourth example may also use an exterior sleeve 53 as described in other examples.

Fifth Example—Alternative Concave Clamp

A fifth example with concave clamp surfaces 7, 9 will be described with reference to FIGS. 60 to 63. This example includes a lead anchor 1 with a first clamping element 17 providing the first clamping surface 7 and a second clamping element 19 providing the second clamping surface 9. The clamping surfaces 7, 9 each have respective concave arcuate cross sections that correspond to the outer surface 25 of the lead 3 as illustrated in FIG. 61. The corresponding shape of the clamping surfaces 7, 9 and the surface of the lead 3 assists in reducing, or preventing, clamping force 13 acting directly through the clamping axis 43. This reduces the likelihood of the force deforming the lead 3 such that the lead lumen 5 is crushed, or otherwise damaging the lead 3.

Figure 62:
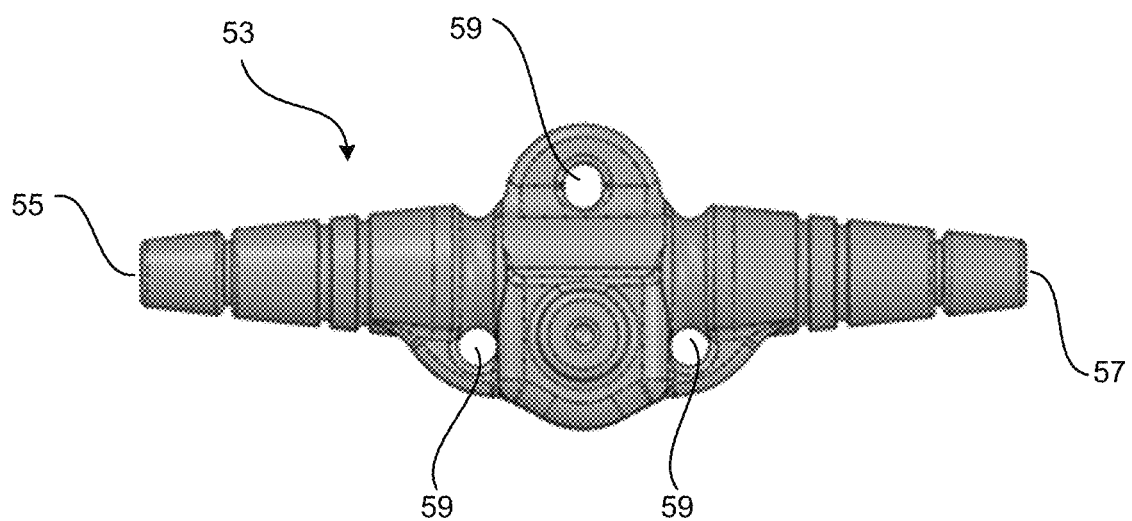
FIG. 62 is a top view of the lead anchor in accordance with the fifth example including the exterior sleeve.

The fifth example can include use of an exterior sleeve 53 as illustrated in FIG. 62.

Sixth Example

Figure 66:
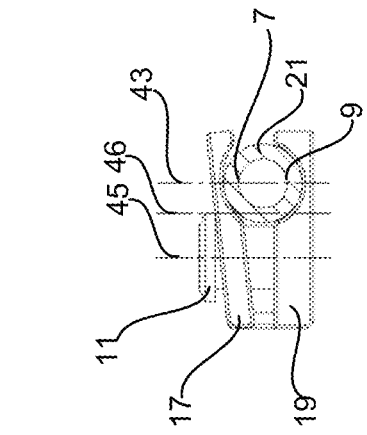
FIG. 66 is a sectioned view of the sixth example of FIG. 65.
Figure 65:
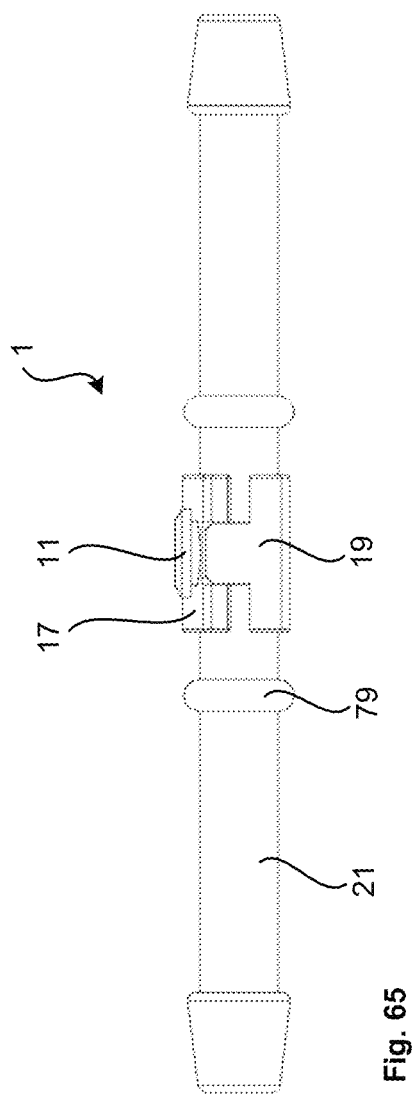
FIG. 65 is a side view of a sixth example of the clamping elements and interior sleeve.

FIGS. 65 and 66 illustrate a sixth example of the lead anchor 1 with an interior sleeve 21, first clamping element 17, second clamping element 19 and a fastener 11. In this example, the first clamping element 17 and second clamping element 19 do not move parallel with respect to each other when the fastener 11 is tightened. In particular, the fastener axis 45 is different to an impingement axis 46. The impingement axis 46 is a corresponding parallel axis where a surface of the fastener 11 acts on the first clamping element 17. This is turn is different to the clamping axis 43, which is the parallel axis that the clamping elements 17, 19 act on the interior sleeve 21 to provide the clamp force to the first and second clamp surfaces 7, 9.

Figure 67:
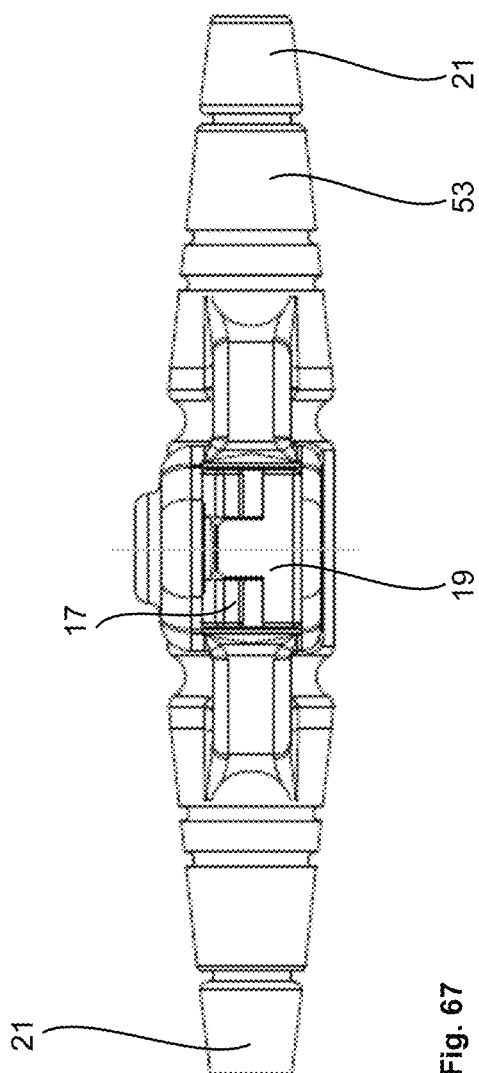
FIG. 67 is a side view of the sixth example with an outer sleeve.

The sixth example can also include use of an exterior sleeve 53 as illustrated in FIG. 67.

Variations and Alternatives

In some variations the first clamp surface 7 and/or the second clamp surface 9 includes a ribbed surface to aid grip to the stimulation lead 3. In other variations, at least part of the stimulation lead 3 has a ribbed outer surface to grip and/or engage with the first and/or second clamp surfaces 7, 9.

In some examples, the functions of the exterior sleeve 53 and interior sleeve 21 are provided by a single common component. Such a common component may be integrally formed or joined together. For example, in some examples the exterior sleeve 53 may be friction welded to the interior sleeve 21 component using ultrasound, thermal energy, etc.

In yet further variations the interior sleeve 21 may engage with the first and/or second clamping elements 17, 19 at an interface comprising at least one ribbed surface. In some examples, both the exterior surface of the interior sleeve 21 and the surfaces of the clamping elements 17, 19 are ribbed to engage with each other. In yet other examples, a shaft and collar arrangement is provide so that the interior sleeve 21 is secured relative to the clamping elements 17, 19 to stop relative movement along the axis of the interior sleeve 21.

In some of the above mentioned examples, the exterior sleeve 53 includes suture loops 59. However, it is to be appreciated that in alternative examples (including those without an exterior sleeve in a configuration similar to FIGS. 7 to 10), suture loops can be provided on other components of the lead anchor 1 including the clamping elements 17, 19, the adjustable fastener 9 and/or the interior sleeve 21.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A lead anchor to secure a stimulation lead with an internal lead lumen, the lead anchor comprising:
   a first clamping element, wherein a first clamp surface is on the first clamping element;
   a second clamping element, wherein a second clamp surface is on the second clamping element and the second clamp surface is opposed to the first clamp surface;
   an adjustable fastener configured to selectively move the first clamping element relative to the second clamping element to draw the first clamp surface towards the second clamp surface to secure the stimulation lead located between the first clamp surface and the second clamp surface; and
   an exterior sleeve that captures the first clamping element, the second clamping element and the adjustable fastener;
   wherein the exterior sleeve comprises a pocket in which the first clamping element, the second clamping element and the adjustable fastener are located;
   wherein the first clamping element is slidingly engaged with the second clamping element to:
   (i) enable relative movement of the first clamp surface towards the second clamp surface along a clamping axis; and
   (ii) restrict relative movement of the first clamp surface and the second clamp surface around the clamping axis;
   wherein the first clamp surface and the second clamp surface are profiled to apply clamping force to secure the stimulation lead while maintaining an open internal lead lumen;

wherein at least one of the first clamping element and the second clamping element includes an arcuate concave surface; and wherein the first clamping element, the second clamping element and the adjustable fastener are insertable into the pocket, wherein the pocket is sealable by a door to capture the first clamping element, the second clamping element, and the adjustable fastener.

2. A lead anchor according to claim 1, wherein the first clamping element is slidingly engaged to the second clamping element with a tongue and groove.

3. A lead anchor according to claim 1, wherein the adjustable fastener selectively draws the first clamping element to the second clamping element along a fastener axis that is substantially parallel to the clamping axis, and wherein the fastener axis does not pass through the first clamp surface nor the second clamp surface.

4. A lead anchor according to claim 1, wherein the arcuate concave surface is configured to receive an outer surface of the stimulation lead.

5. A lead anchor according to claim 4, wherein a cross section of the arcuate concave surface has a radius of curvature corresponding to a radius of curvature of the outer surface of the stimulation lead.

6. A lead anchor according to claim 1, wherein a cross section of the arcuate concave surface has a radius of curvature greater than a radius of curvature of the internal lead lumen of the stimulation lead.

7. A lead anchor according to claim 1, wherein the adjustable fastener includes a threaded fastener.

8. A lead anchor according to claim 1, wherein the first clamp surface and/or the second clamp surface includes a ribbed surface to aid grip to the stimulation lead.

9. A lead anchor according to claim 1, further comprising at least one ramp or chamfer leading to the first clamp surface and second clamp surface to assist insertion of the stimulation lead between the first clamp surface and the second clamp surface before the adjustable faster selectively draws the first clamp surface to the second clamp surface.

10. A lead anchor according to claim 1, further comprising one or more stops to maintain the first clamping surface and the second clamping surface at a specified minimum distance.

11. A lead anchor according to claim 1, wherein the exterior sleeve comprises a plurality of extensions, and each of the plurality of extensions extend away from the pocket,
wherein each of the plurality of extensions comprises an internal passage that enables the stimulation lead to pass through the exterior sleeve and through the pocket of the exterior sleeve.

12. A lead anchor according to claim 11, wherein each of the plurality of extensions are tapered and terminate in a respective aperture for the stimulation lead to pass through.

* * * * *